(12) United States Patent
Lee et al.

(10) Patent No.: US 7,532,934 B2
(45) Date of Patent: May 12, 2009

(54) SNORING DETECTION SYSTEM AND METHOD

(75) Inventors: Kent Lee, Fridley, MN (US); John D. Hatlestad, Maplewood, MN (US); Jeffrey E. Stahmann, Ramsey, MN (US); Jesse W. Hartley, Lino Lakes, MN (US); Quan Ni, Shoreview, MN (US); Krzysztof J. Siejko, Maple Grove, MN (US)

(73) Assignee: Cardiac Pacemakers, Inc., St. Paul, MN (US)

( * ) Notice: Subject to any disclaimer, the term of this patent is extended or adjusted under 35 U.S.C. 154(b) by 598 days.

(21) Appl. No.: 10/943,071

(22) Filed: Sep. 15, 2004

(65) Prior Publication Data

US 2005/0065560 A1  Mar. 24, 2005

Related U.S. Application Data

(60) Provisional application No. 60/504,046, filed on Sep. 18, 2003.

(51) Int. Cl.
*A61N 1/40* (2006.01)
(52) U.S. Cl. .......................................... 607/42; 607/17
(58) Field of Classification Search ................ 607/42, 607/17
See application file for complete search history.

(56) References Cited

U.S. PATENT DOCUMENTS

| | | | |
|---|---|---|---|
| 4,365,636 A | 12/1982 | Barker | |
| 4,562,841 A | 1/1986 | Brockway et al. | |
| 4,813,427 A | 3/1989 | Schlaefke et al. | |
| 4,830,008 A | 5/1989 | Meer | |
| 4,982,738 A | 1/1991 | Griebel | |
| 5,036,849 A | 8/1991 | Hauck et al. | |
| 5,105,354 A | 4/1992 | Nishimura | |
| 5,123,425 A | 6/1992 | Shannon, Jr. et al. | |
| 5,146,918 A | 9/1992 | Kallok et al. | |
| 5,203,348 A | 4/1993 | Dahl et al. | |
| 5,211,173 A | 5/1993 | Kallok et al. | |

(Continued)

FOREIGN PATENT DOCUMENTS

EP  0 940 155 A  8/1999

(Continued)

OTHER PUBLICATIONS

Balaban et al., *Feasibility of Screening for Sleep Apnea Using Pacemaker Impedance Sensor*, NASPE (2001).

(Continued)

*Primary Examiner*—Carl H Layno
*Assistant Examiner*—Deborah Malamud
(74) *Attorney, Agent, or Firm*—Hollingsworth & Funk, LLC

(57) ABSTRACT

Systems and methods provide for detecting snoring, and for determining the presence of sleep disordered breathing using detected snoring. Snoring indicative signals generated by one or more patient-internal or external sensors are detected. The presence of sleep disordered breathing is algorithmically determined, patient-internally or externally, using the snoring signals. Algorithmically determining presence of sleep disordered breathing may include computing a snoring index developed from the detected snoring. Sleep apnea may be detected using the snoring index. Sleep apnea may be verified using internal or external sensors. A positive airway pressure device may operate cooperatively to verify and treat sleep disordered breathing.

25 Claims, 20 Drawing Sheets

U.S. PATENT DOCUMENTS

| | | | |
|---|---|---|---|
| 5,215,082 A | 6/1993 | Kallok et al. | |
| 5,230,337 A | 7/1993 | Dahl et al. | |
| 5,233,983 A | 8/1993 | Markowitz | |
| 5,259,373 A | 11/1993 | Gruenke et al. | |
| 5,284,136 A | 2/1994 | Hauck et al. | |
| 5,313,953 A | 5/1994 | Yomtov et al. | |
| 5,360,442 A | 11/1994 | Dahl et al. | |
| 5,366,496 A | 11/1994 | Dahl et al. | |
| 5,376,476 A | 12/1994 | Eylon | |
| 5,388,578 A | 2/1995 | Yomtov et al. | |
| 5,391,200 A | 2/1995 | KenKnight et al. | |
| 5,397,342 A | 3/1995 | Heil, Jr. et al. | |
| 5,411,031 A | 5/1995 | Yomtov | |
| 5,483,969 A | 1/1996 | Testerman et al. | |
| 5,485,851 A | 1/1996 | Erickson | |
| 5,522,862 A | 6/1996 | Testerman et al. | |
| 5,540,727 A | 7/1996 | Tockman et al. | |
| 5,545,202 A | 8/1996 | Dahl et al. | |
| 5,549,655 A | 8/1996 | Erickson | |
| 5,603,732 A | 2/1997 | Dahl et al. | |
| 5,738,102 A | 4/1998 | Lemelson | |
| 5,814,087 A | 9/1998 | Renirie | |
| 5,836,987 A | 11/1998 | Baumann et al. | |
| 5,844,680 A | 12/1998 | Sperling | |
| 5,861,011 A | 1/1999 | Stoop | |
| 5,891,023 A | 4/1999 | Lynn | |
| 5,911,218 A | 6/1999 | DiMarco | |
| 5,916,243 A | 6/1999 | KenKnight et al. | |
| 5,970,975 A * | 10/1999 | Estes et al. | 128/204.23 |
| 5,974,340 A | 10/1999 | Kadhiresan | |
| 6,044,298 A | 3/2000 | Salo et al. | |
| 6,055,454 A | 4/2000 | Heemels | |
| 6,064,910 A | 5/2000 | Andersson et al. | |
| 6,091,973 A | 7/2000 | Colla et al. | |
| 6,099,479 A | 8/2000 | Christopherson et al. | |
| 6,120,441 A | 9/2000 | Griebel | |
| 6,126,611 A | 10/2000 | Bourgeois et al. | |
| 6,128,534 A | 10/2000 | Park et al. | |
| 6,132,384 A | 10/2000 | Christopherson et al. | |
| 6,141,590 A | 10/2000 | Renirie et al. | |
| 6,221,011 B1 | 4/2001 | Bardy | |
| 6,240,316 B1 | 5/2001 | Richmond et al. | |
| 6,251,126 B1 | 6/2001 | Ottenhoff et al. | |
| 6,269,269 B1 | 7/2001 | Ottenhoff et al. | |
| 6,270,457 B1 | 8/2001 | Bardy | |
| 6,272,377 B1 | 8/2001 | Sweeney et al. | |
| 6,275,727 B1 | 8/2001 | Hopper et al. | |
| 6,277,072 B1 | 8/2001 | Bardy | |
| 6,280,380 B1 | 8/2001 | Bardy | |
| 6,312,378 B1 | 11/2001 | Bardy | |
| 6,336,903 B1 | 1/2002 | Bardy | |
| 6,358,203 B2 | 3/2002 | Bardy | |
| 6,363,270 B1 | 3/2002 | Colla et al. | |
| 6,368,284 B1 | 4/2002 | Bardy | |
| 6,398,728 B1 | 6/2002 | Bardy | |
| 6,415,183 B1 | 7/2002 | Scheiner et al. | |
| 6,440,066 B1 | 8/2002 | Bardy | |
| 6,459,929 B1 | 10/2002 | Hopper et al. | |
| 6,574,507 B1 | 6/2003 | Bonnet | |
| 6,589,188 B1 | 7/2003 | Street et al. | |
| 6,641,542 B2 | 11/2003 | Cho et al. | |
| 6,773,404 B2 | 8/2004 | Poezevera et al. | |
| 2002/0193839 A1 | 12/2002 | Cho et al. | |
| 2003/0023184 A1 | 1/2003 | Pitts-Crick et al. | |
| 2003/0100925 A1 | 5/2003 | Pape et al. | |
| 2003/0153953 A1 | 8/2003 | Park et al. | |
| 2003/0153954 A1 | 8/2003 | Park et al. | |
| 2003/0153955 A1 | 8/2003 | Park et al. | |
| 2003/0153956 A1 | 8/2003 | Park et al. | |
| 2003/0195571 A1 | 10/2003 | Burnes et al. | |
| 2003/0199945 A1 | 10/2003 | Ciulla | |
| 2003/0204213 A1 | 10/2003 | Jensen et al. | |
| 2003/0216789 A1 * | 11/2003 | Deem et al. | 607/9 |
| 2004/0002742 A1 | 1/2004 | Florio | |
| 2004/0030362 A1 | 2/2004 | Hill et al. | |
| 2004/0088027 A1 | 5/2004 | Burnes et al. | |
| 2004/0138719 A1 | 7/2004 | Cho et al. | |
| 2004/0210261 A1 * | 10/2004 | King et al. | 607/9 |

FOREIGN PATENT DOCUMENTS

| | | |
|---|---|---|
| WO | 99/04841 | 2/1999 |
| WO | WO 00/17615 | 3/2000 |
| WO | 02/087696 | 7/2002 |

OTHER PUBLICATIONS

Bradley et al., Pathophysiologic and Therapeutic Implications of Sleep Apnea in Congestive Heart Failure, 3 J. Cardiac Failure 223-240 (1996). Abstract only.

Bradley et al., Sleep Apnea and Heart Failure, Park I: Obstructive Sleep Apnea, 107 Circulation 1671-1678 (2003).

Lugaresi et al., Snoring, 39 Electroencephalogr. Clin. Neurophysiol. 59-64 (1975). Abstract only.

Garrigue et al., Night Atrial Overdrive with DDD Pacing Results in a Significant Reduction of Sleep Apnea Episodes and QOL Improvement in Heart Failure Patients, NASPE (2001).

Garrigue et al., Benefit of Atrial Pacing in Sleep Apnea Syndrome, 346 N. Engl. J. Med. 404-412 (2002). Abstract only.

Hilton et al., Evaluation of Frequency and Time-frequency Spectral Analysis of Heart Rate Variability as a Diagnostic Marker of the Sleep Apnea Syndrome, 37 Med. Biol. Eng. Comput. 760-769 (1999). Abstract only.

Jais et al., Night Atrial Overdrive with DDD Pacing: a New Therapy for Sleep Apnea Syndrome, NASPE (2000).

Javaheri et al., Sleep Apnea in 81 Ambulatory Male Patients with Stable Heart Failure: Types and Their Prevalences, Consequences, and Presentations, 97 Circulation 2154-2159 (1998).

Olusola et al., Nightcap: Laboratory and home-based evaluation of a portable sleep monitor, 32 Psychophysiology, 32-98 (1995). Abstract only.

Verrier et al., Sleep, dreams, and sudden death: the case for sleep as an autonomic stress test for the heart, 31 Cardiovascular Research 181-211 (1996).

Verrier et al., Sleep Related Cardiovascular Risk: New Home-Based Monitoring Technology for Improved Diagnosis and Therapy, 2 A.N. E. 158-175 (1997).

Roche et al., Screening of Obstructive Sleep Apnea Syndrome by Heart Rate Variability Analysis, 100 Circulation 1411-1455 (1999).

Shahrokh, A Mechanism of Central Sleep Apnea In Patients With Heart Failure, 341 N. Engl. J. Med. 949-954 (1999). Abstract only.

Vanninen et al., Cardiac Sympathovagal Balance During Sleep Apnea Episodes, 16 Clin. Physiol. 209-216 (1996). Abstract only.

Waldemark et al., Detection of Apnea using Short Window FFT Technique and Artificial Neural Network, 3390 SPIE International Society for Optical Engineering 122-133 (1998).

Young et al., The Occurrence of Sleep-Disordered Breathing Among Middle Aged Adults, N. Engl. J. Med. 1230-1235 (1993). Abstract only.

* cited by examiner

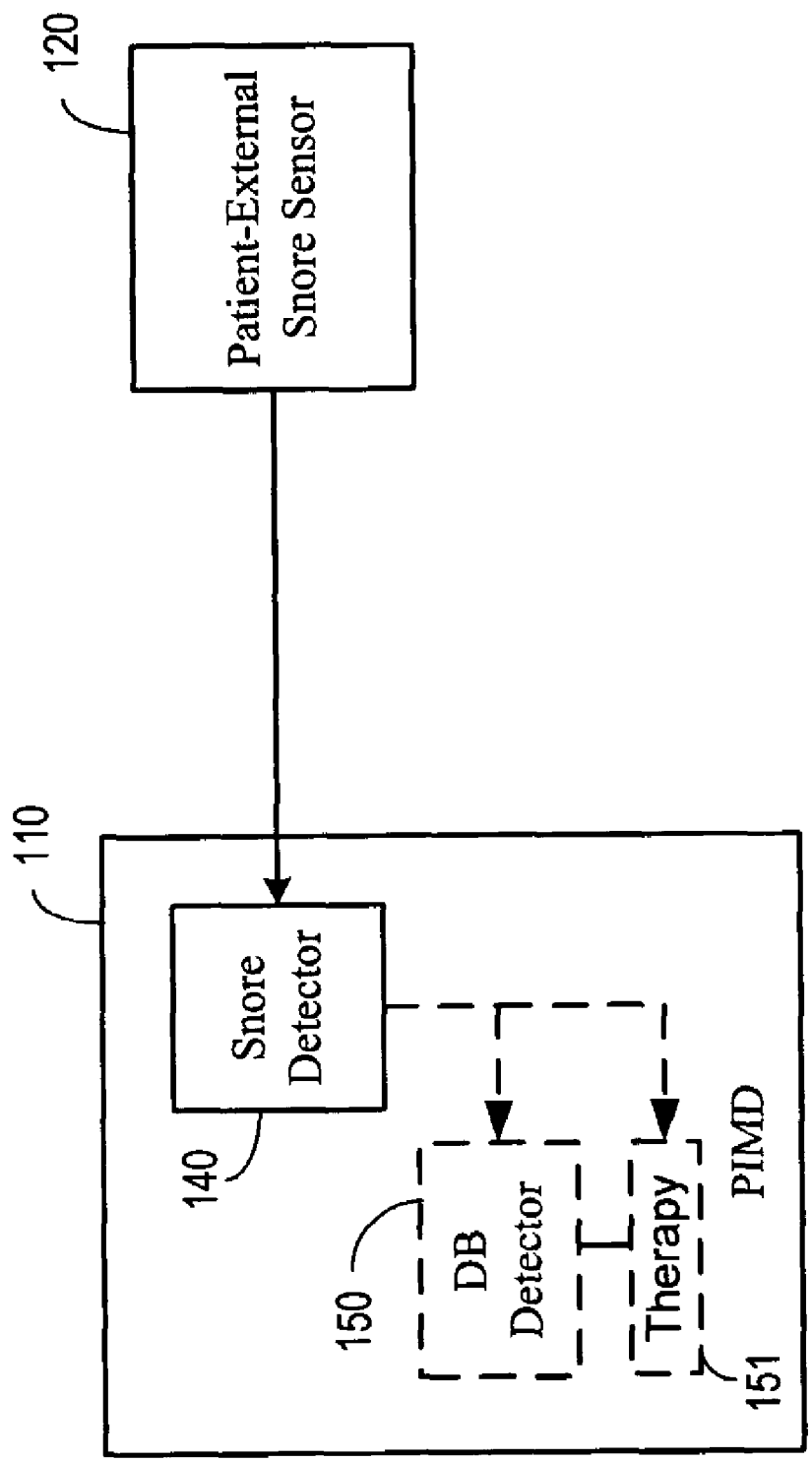

SNORING DETECTION SYSTEM AND METHOD

RELATED PATENT DOCUMENTS

This application claims the benefit of Provisional Patent Application Ser. No. 60/504,046, filed on Sep. 18, 2003, to which priority is claimed pursuant to 35 U.S.C. §119(e) and which is hereby incorporated herein by reference in its entirety.

FIELD OF THE INVENTION

The present invention relates generally to systems and methods for detecting snoring.

BACKGROUND OF THE INVENTION

Disordered breathing refers to a wide spectrum of respiratory disorders that involve disruption of the normal respiratory cycle. Although disordered breathing typically occurs during sleep, the disorder may also occur while the patient is awake. Unfortunately, disordered breathing is often undiagnosed. If left untreated, the effects of disordered breathing may result in serious health consequences for the patient.

Apnea is a fairly common breathing disorder characterized by periods of interrupted breathing. Apnea is typically classified based on its etiology. One type of apnea, denoted obstructive apnea, occurs when the patient's airway is obstructed by the collapse of soft tissue in the rear of the throat. Central apnea is caused by a derangement of the central nervous system control of respiration. The patient ceases to breathe when control signals from the brain to the respiratory muscles are absent or interrupted. Mixed apnea is a combination of the central and obstructive apnea types. Regardless of the type of apnea, people experiencing an apnea event stop breathing for a period of time. The cessation of breathing may occur repeatedly during sleep, sometimes hundreds of times a night and sometimes for a minute or longer.

In addition to apnea, other types of disordered respiration have been identified, including hypopnea (shallow breathing), tachypnea (rapid breathing), hyperpnea (heavy breathing), and dyspnea (labored breathing). Combinations of the respiratory cycles described above may be observed, including, for example, periodic breathing and Cheyne-Stokes breathing. Periodic breathing is characterized by cyclic respiratory patterns that may exhibit rhythmic rises and falls in tidal volume. Cheyne-Stokes respiration is a specific form of periodic breathing wherein the tidal volume decreases to zero resulting in apneic intervals. The breathing interruptions of periodic breathing and CSR may be associated with central apnea, or may be obstructive in nature. CSR is frequently observed in patients with congestive heart failure (CHF) and is associated with an increased risk of accelerated CHF progression. Because of the cardiovascular implications, therapy for respiration-related sleep disorders is of particular interest.

Disordered breathing affects a significant percentage of people. Sleep disordered breathing is particularly prevalent and is associated with excessive daytime sleepiness, systemic hypertension, increased risk of stroke, angina and myocardial infarction. Respiratory disruption can be particularly serious for patients concurrently suffering from cardiovascular deficiencies, such as congestive heart failure.

Snoring may indicate the presence of sleep disordered breathing. Snoring has been correlated with obstructive sleep apnea. Collapse of the soft tissue in the upper airway during an apnea event causes the airway to vibrate, resulting in snoring. Furthermore, snoring may be correlated to hypertension caused by frequent arousals from sleep, reductions in oxygen saturation, increased respiratory effort, and/or increases in thoracic pressure. Thus, detection of frequent snoring may aid in the diagnosis of patients at risk for hypertension and other pathological disorders.

Nighttime snoring may cause an increase in inspiratory effort and reduction in tidal volume, leading to frequent arousals from sleep. Frequent arousals from sleep lead to sleep fragmentation, separate from any underlying disordered breathing. Sleep fragmentation leads to fatigue and sleepiness.

SUMMARY OF THE INVENTION

The present invention is directed to systems and methods for detecting snoring, and for determining the presence of sleep disordered breathing using detected snoring. According to one embodiment, snoring sounds generated by a patient are detected. The presence of sleep disordered breathing is determined using the detected snoring sounds. In another embodiment, snoring is detected from disturbances in a respiration or airflow signal.

Snoring sounds or snoring-related respiration/airflow disturbances may be detected internally of the patient or externally of the patient. Determining presence of sleep disordered breathing may be performed internally or externally of the patient. Determining presence of sleep disordered breathing may include computing a snoring index developed from the detected snoring. Sleep apnea may be detected using the snoring index. Sleep apnea may be verified using internal or external sensors. In one approach, sleep disordered breathing is detected, such as by use of a minute ventilation sensor, and presence of the sleep disordered breathing may be confirmed using the detected snoring.

Embodiments of methods of detecting snoring in a patient in accordance with the present invention involve generating a signal modulated by snoring and detecting snoring based on the generated signal, wherein at least one of generating the signal and detecting snoring is performed using a component disposed in or on a cardiac rhythm management device. Modulating the signal by snoring and detecting snoring may be performed implantably, such as by using a sensor disposed in or on a pulse generator housing. The sensor may alternately or additionally be disposed in or on a lead system coupled to a pulse generator, in or on a header of a pulse generator, coupled to a cardiac rhythm management system, mechanically coupled to an external respiration therapy device, or disposed in or on a respiratory mask. Detecting snoring may involve using circuitry disposed in or on a cardiac rhythm management device, which may further deliver a therapy to mitigate the detected snoring, and/or detect sleep disordered breathing based on the detected snoring, and/or deliver a therapy to treat the detected disordered breathing.

According to another embodiment, a system includes a sensor configured to sense snoring generated by a patient and a processor coupled to the sensor. The processor algorithmically determines presence of sleep disordered breathing using the sensed snoring. The sensor may include one or more of an accelerometer, a microphone, a pressure transducer, a subsonic sensor, a respiration sensor, or a vibration or motion sensor. The sensor may be implemented for patient-external sensing of the snoring or on or within an implantable sensing device. The processor may be disposed within an implantable medical device (e.g., CRM device).

The system may further include a positive airway pressure (CPAP) device communicatively coupled to one or both of the sensor and the processor. Sleep disordered breathing may be verified using the CPAP device.

The above summary of the present invention is not intended to describe each embodiment or every implementation of the present invention. Advantages and attainments, together with a more complete understanding of the invention, will become apparent and appreciated by referring to the following detailed description and claims taken in conjunction with the accompanying drawings.

BRIEF DESCRIPTION OF THE DRAWINGS

FIGS. 1A and 1B are block diagrams of implantable systems implementing snoring detection and therapy features in accordance with embodiments of the present invention;

Figure 1B:
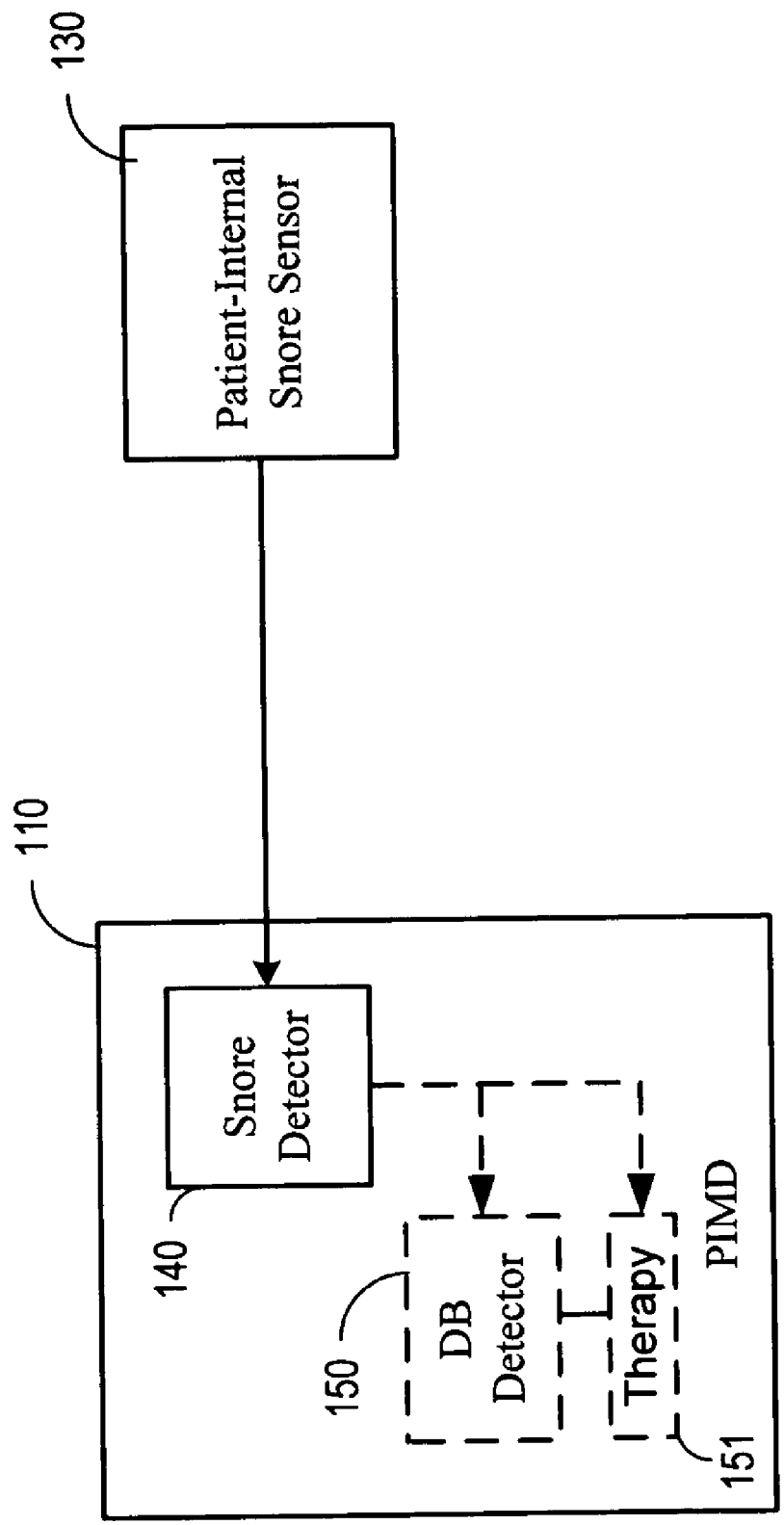

While the invention is amenable to various modifications and alternative forms, specifics thereof have been shown by way of example in the drawings and will be described in detail below. It is to be understood, however, that the intention is not to limit the invention to the particular embodiments described. On the contrary, the invention is intended to cover all modifications, equivalents, and alternatives falling within the scope of the invention as defined by the appended claims.

DETAILED DESCRIPTION OF VARIOUS EMBODIMENTS

In the following description of the illustrated embodiments, references are made to the accompanying drawings, which form a part hereof, and in which are shown by way of illustration, various embodiments by which the invention may be practiced. It is to be understood that other embodiments may be utilized, and structural and functional changes may be made without departing from the scope of the present invention.

The present invention is directed to one or more of sensing, detection, and treatment of snoring using an at least partially implantable device. Snoring information is useful in disordered breathing detection, verification, and/or prediction, such as for detecting apnea events. Snoring detection is also useful independent of disordered breathing, to treat the snoring itself. Snoring may lead to insomnia, arousals from sleep, marital discord, and wake-time sleepiness. Snoring detection in accordance with the present invention may also be used to treat the snoring, such as by modulating the pressure of a continuous positive airway pressure (CPAP) device to reduce the snoring, for example.

An internal or external snore sensor, such as a vibration sensor, respiration sensor, airflow sensor, accelerometer or microphone, may be coupled to a patient-internal medical device (PIMD), such as a cardiac rhythm management (CRM) device, or a respiration therapy device. In one embodiment, the snore sensor may be configured as a patient-external device, possibly mounted on a respiratory mask, for example. Information from the snore sensor is wirelessly transmitted to the PIMD device.

In another embodiment, the snore sensor may be associated with an implanted device, such as an accelerometer positioned within or on the housing of an PIMD device, or on the PIMD lead system. A snore detector in the PIMD device may receive signals from the patient-external and/or patient-internal snore sensor, and may generate one or more snore indices, based on the frequency, severity and/or other characteristics of snoring incidents, for example. A snore index may be used, for example, to determine if a patient is at risk for daytime fatigue and sleepiness due to excessive nighttime snoring indicating sleep disordered breathing.

In another embodiment, an airflow sensor may be associated with an implanted device, such as a transthoracic impedance sensor mounted on the lead system of a PIMD device. The snore detector in the PIMD device may be configured to algorithmically detect snoring using the transthoracic impedance signal, and may be configured to generate one or more snoring indices. For example, airflow may be measured, such as by use of transthoracic impedance or external airflow sensing, and snoring may be determined using the airflow measurement.

Detection of the snore severity, as measured by a severity snore index, may be used to test for risk of vascular disease such as hypertension. A snore index also may be used in connection with disordered breathing detection and/or prediction. One or more snore indices may be stored, trended, displayed and/or transmitted to another device.

A significant percentage of patients between the ages of 30 and 60 years experience some symptoms of disordered breathing. Although disordered breathing may occur while the patient is awake, it more often occurs during sleep. Sleep disordered breathing is associated with excessive daytime sleepiness, systemic hypertension, increased risk of stroke, angina, and myocardial infarction. Disordered breathing is particularly prevalent among congestive heart failure patients, and may contribute to the progression of heart failure.

Various therapies have been used to treat central and/or obstructive disordered breathing episodes. Obstructive sleep apnea has been associated with prolapse of the tongue and its surrounding structure into the pharynx, thus occluding the respiratory pathway. A commonly prescribed treatment for obstructive apnea uses CPAP therapy.

A typical CPAP device delivers air pressure through a nasal mask worn by the patient. The application of continuous positive airway pressure keeps the patient's throat open, reducing or eliminating the obstruction causing apnea. Positive airway pressure devices may be used to provide a variety of respiration therapies, including, for example, continuous positive airway pressure (CPAP), bi-level positive airway pressure (bi-level PAP), proportional positive airway pressure (PPAP), auto-titrating positive airway pressure, ventilation, gas or oxygen therapies. Some positive airway pressure devices may also be configured to provide both positive and negative pressure, such that negative pressure is selectively used (and de-activated) when necessary, such as when treating Cheyne-Stokes breathing, for example. The term CPAP will be used herein as a generic term for any such device, including devices using forms of positive airway pressure (and negative pressure when necessary), whether continuous or otherwise.

Disorders and diseases affecting the interdependent physiological systems of the human body may be more effectively diagnosed and treated using a coordinated approach. Various embodiments of the invention are implemented using medical systems employing one or a number of patient-external and/or patient-internal medical devices. Medical devices may communicate or otherwise operate in concert or in a stand-alone manner to provide more comprehensive patient monitoring, diagnosis, and therapy.

As will be further described below, additional sensors, such as accelerometers or other motion sensors and/or posture sensors, may be used to confirm or verify the detection of a sleep apnea or hypopnea episode by using snoring information. The additional sensors may also be employed to prevent false or missed detections of sleep apnea/hypopnea due to posture and/or motion related artifacts.

FIGS. 1A and 1B illustrate embodiments of the present invention involving snoring detection using an implantable device. The processes and systems exemplified by these embodiments may be implemented alone or in combination with one or more processes and systems exemplified by other embodiments described herein to provide a coordinated approach to patient monitoring, diagnosis, and/or therapy.

In various embodiments, the snore sensor may be implantable, partially implantable, or patient-external. The snore sensor may be coupled to detection circuitry directly, coupled through wiring, and/or coupled wirelessly. The sensor may be incorporated into a lead, such as a cardiac pacing lead.

In accordance with embodiments of the invention, illustrated in FIGS. 1A and 1B, a snore sensor 120 (FIG. 1A) and 130 (FIG. 1B), such as an accelerometer or microphone, is coupled to a PIMD device 110 and used for snoring detection. In one embodiment (FIG. 1A), the snore sensor 120 is a patient-external device, possibly mounted on a CPAP mask housing, for example. Information from the snore sensor 120 is wirelessly transmitted to the PIMD device 110.

In another embodiment (FIG. 1B), the snore sensor 130 is an implanted device, such as, for example, an accelerometer or a transthoracic impedance sensor positioned within or on the housing of the PIMD device 110, or on a PIMD lead system (not shown). For example, the low frequency sounds produced by snoring can be detected using a PIMD accelerometer, such as an accelerometer used in connection with rate adaptive pacing or posture sensing, for example. By way of further example, disturbances in a transthoracic impedance sensor signal indicative of snoring may be detected.

According to a further embodiment, the snore sensor 120/130 may be implemented as an airflow sensor configured to sense airflow disturbances indicative of snoring. The snore sensor 120/130 may be implemented as an internal or an external airflow sensor. For example, the snore sensor 130 may be implemented as an external airflow sensor, which may be provided on a CPAP mask, and configured to sense patient snoring.

A snore detector 140 in the PIMD device 110 receives signals from the patient-external snore sensor 120 and/or patient-internal snore sensor 130, and may generate one or more snore indices, based on the frequency, severity and/or other characteristics of snoring incidents, for example. Snoring detection in accordance with embodiments of the invention may be used alone, or in combination with other sensors, to detect and/or verify occurrences of disordered breathing. For example, detection of periodic snorts may indicate an episode of obstructive sleep apnea.

The snoring methodology described herein may be used in cooperation with a multi-sensor system. Snore information may be used in combination with information from other patient-internal and/or patient-external sensors to confirm the detection of disordered breathing. In accordance with the present invention, any number or all of snoring sensor(s), snoring detector(s), disordered breathing detector(s), and disordered breathing prediction device(s) may be implantable, partially implantable, or patient-external, as long as at least one element is at least partially implantable. In one approach, an initial detection of a disordered breathing episode may be made by an optional disordered breathing detector 150 based on respiration patterns detected using a transthoracic impedance sensor. Snore information may be used alone, or in combination with other sensor signals, to confirm the initial detection of disordered breathing.

In another example, an initial detection of a disordered breathing episode may be made by a CPAP device using a respiration signal acquired from sensors on the CPAP mask. The CPAP device may communicate with the PIMD device 110 for confirmation of disordered breathing. Based on snoring information obtained and evaluated in the PIMD device 110, the PIMD device 110 may confirm or refute the occurrence of disordered breathing and respond accordingly, such as through a change of settings, alarm, or other action.

In another implementation, detection of snoring may be used to modulate CPAP pressure, allowing auto-titration of CPAP pressure therapy through snoring detection. Detection of snoring may indicate that the CPAP pressure is insufficient to open the patient's airways. In accordance with an embodiment of the invention, a CPAP mounted microphone may be used to detect snoring. Based on detection of snoring, or based on snoring characteristics, e.g., the snore index, CPAP pressure may be modulated. For example, the snore index may be compared to a threshold. If the snore index is beyond the threshold, the CPAP pressure may be increased. In another example, CPAP therapy pressure may be adjusted as a function of the snore index. In a further embodiment, optional therapy circuitry 151 may be used to provide therapy to, for example, reduce snoring, correct disordered breathing, improve patient hemodynamics, or other therapy.

Figure 1C:
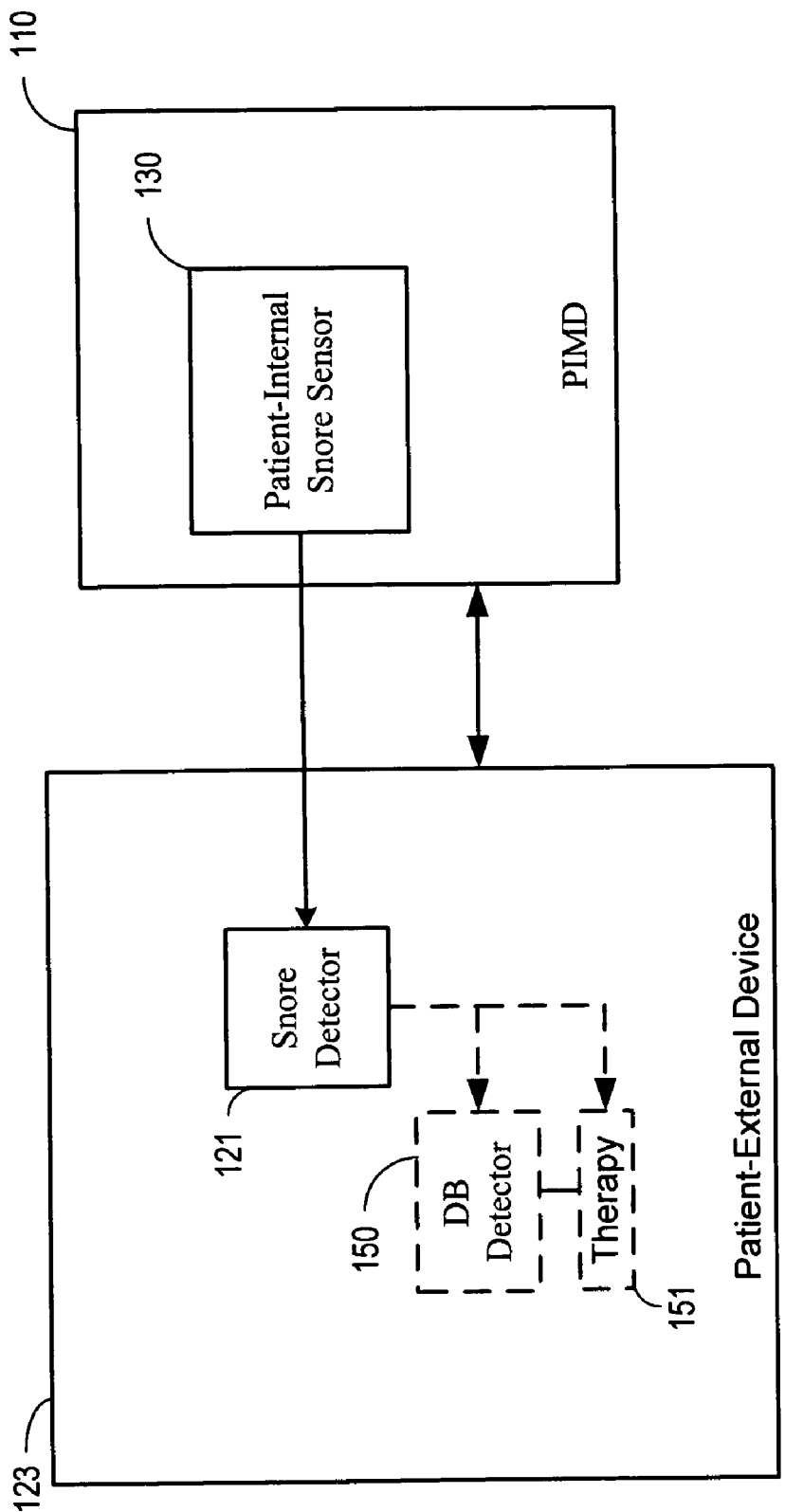
FIGS. 1C and 1D are block diagrams illustrating embodiments of the present invention with a snore detector in a patient-external configuration.
Figure 1D:
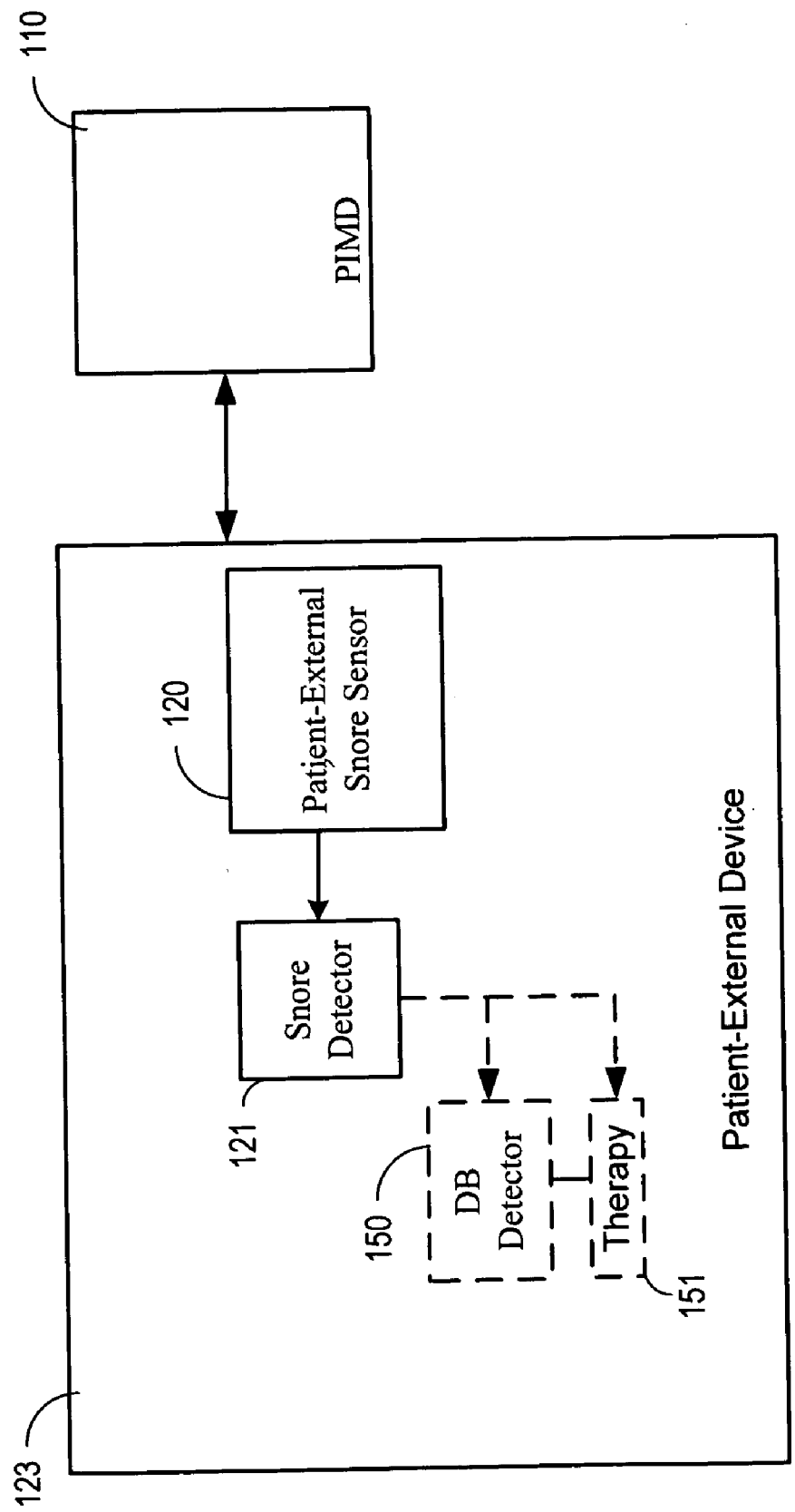

FIGS. 1C and 1D illustrate embodiments of the present invention with a snore detector 121 in a patient-external configuration 123. The snore detector 121 may be coupled to the PIMD device 110 wirelessly, for example. The snore sensor may be an internal snore sensor 130 (FIG. 1C) or a patient-external snore sensor 120 (FIG. 1D), such as of a type previously described. Similarly to the snore detector 121, the disordered breathing detector 150, and therapy circuitry 151 may be implemented in either or both of patient-external and internal configurations, as well as cooperate with the PIMD device 110 for coordinated and/or combined therapy.

Figure 2:
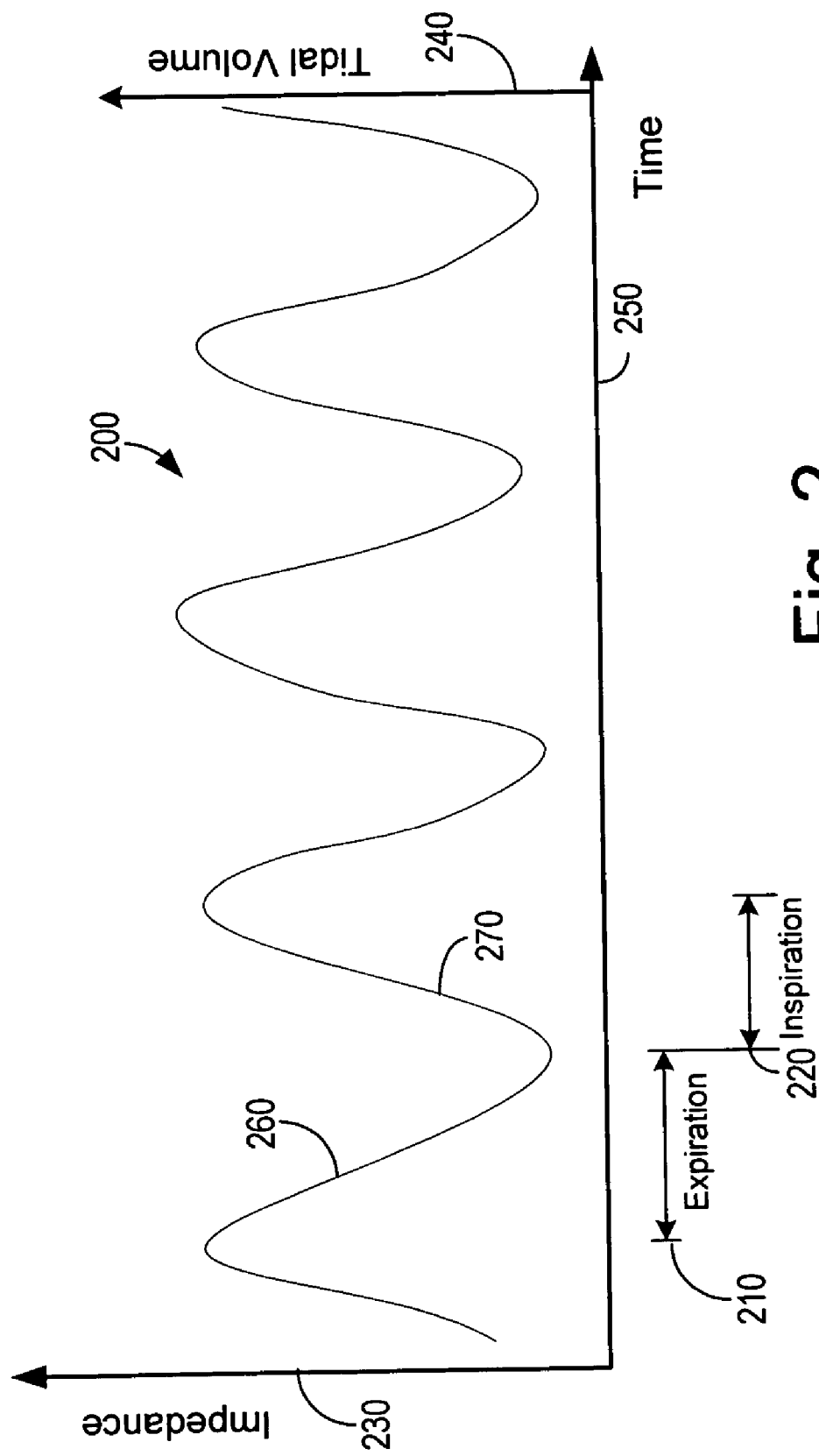
FIG. 2 is a graph of a normal respiration signal measured by a transthoracic impedance sensor that may be utilized for coordinated monitoring, diagnosis and/or therapy in accordance with embodiments of the present invention.

Referring now to FIG. 2, an impedance signal 200 is illustrated. The impedance signal 200 may be developed, for example, from an impedance sense electrode in combination with a PIMD device. The impedance signal 200 is proportional to the transthoracic impedance, illustrated as an impedance 230 on the abscissa of the left side of the graph in FIG. 2. The impedance 230 increases during any respiratory inspiration 220 and decreases during any respiratory expiration 210. The impedance signal 200 is also proportional to the amount of air inhaled, denoted a tidal volume 240, illustrated on the abscissa of the right side of the graph in FIG. 2. The variations in impedance during respiration, identifiable as the peak-to-peak variation of the impedance signal 200, may be used to determine the respiration tidal volume 240, corresponding to the volume of air moved in a breath, one cycle of expiration 210 and inspiration 220. A minute ventilation may also be determined, corresponding to the amount of air moved per a minute of time 250 illustrated on the ordinate of the graph in FIG. 2.

Snoring and other episodes of breathing disorders may be determined using the impedance signal 230, and other information available to the sleep detector circuitry. During non-REM sleep, a normal respiration pattern includes regular, rhythmic inspiration—expiration cycles without substantial interruptions. When the tidal volume (TV) of the patient's respiration, as indicated by the transthoracic impedance signal, falls below a hypopnea threshold, then a hypopnea event is declared. For example, a hypopnea event may be declared if the patient's tidal volume falls below about 50% of a recent average tidal volume or other baseline tidal volume value. If the patient's tidal volume falls further to an apnea threshold, e.g., about 10% of the recent average tidal volume or other baseline value, an apnea event is declared.

Figure 3A:
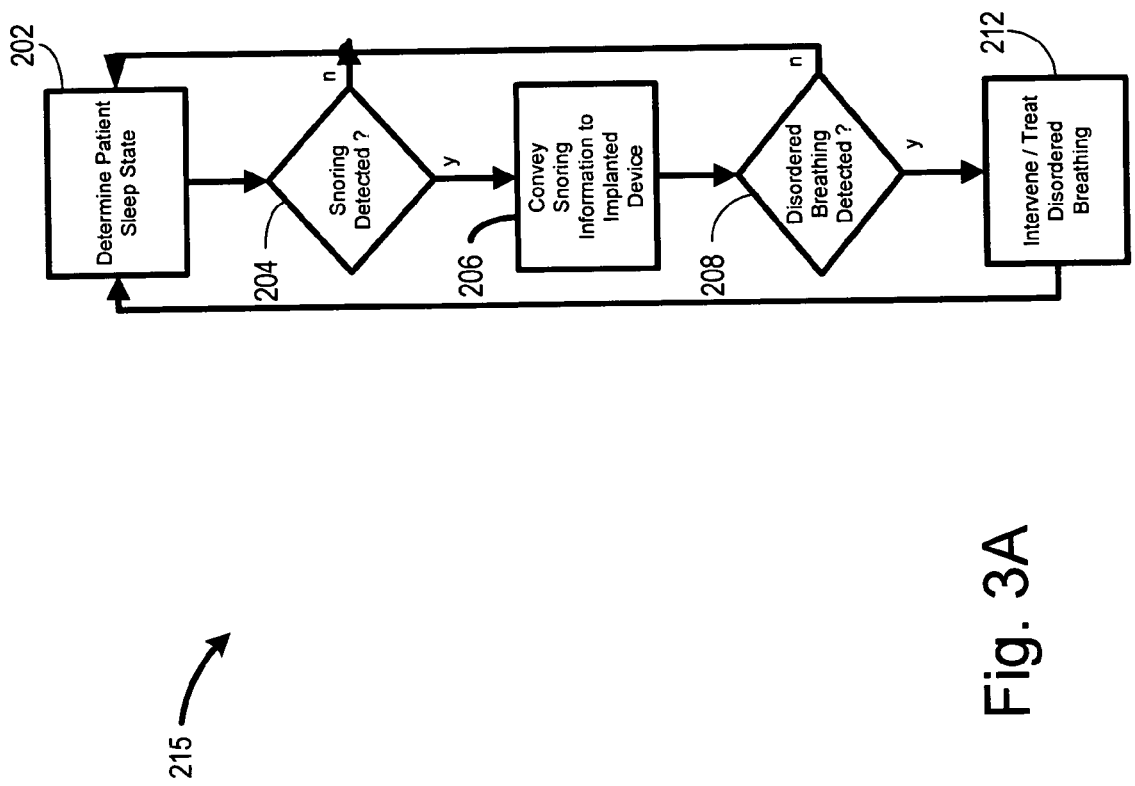
FIG. 3A is a flow chart illustrating a snoring detection algorithm based on signals from an accelerometer in accordance with embodiments of the present invention.

FIG. 3A illustrates an algorithm for a method 215 of determining the presence of sleep disordered breathing using detected snoring. At block 202, a patient's sleep state is determined, as will be further described with reference to FIG. 3B below. If the patient is sleeping, a sensor (internal or external to the patient) is used at block 204 to detect snoring. If snoring is detected, information related to the snoring is conveyed to a PIMD device at block 206.

The snoring information from block 206 is used at block 208 to, for example, predict, verify, classify, and/or determine the severity of a disordered breathing episode. If disordered breathing is detected that requires intervention and/or treatment, the intervention and/or treatment is performed at block 212 before re-starting the method 215.

Figure 3B:
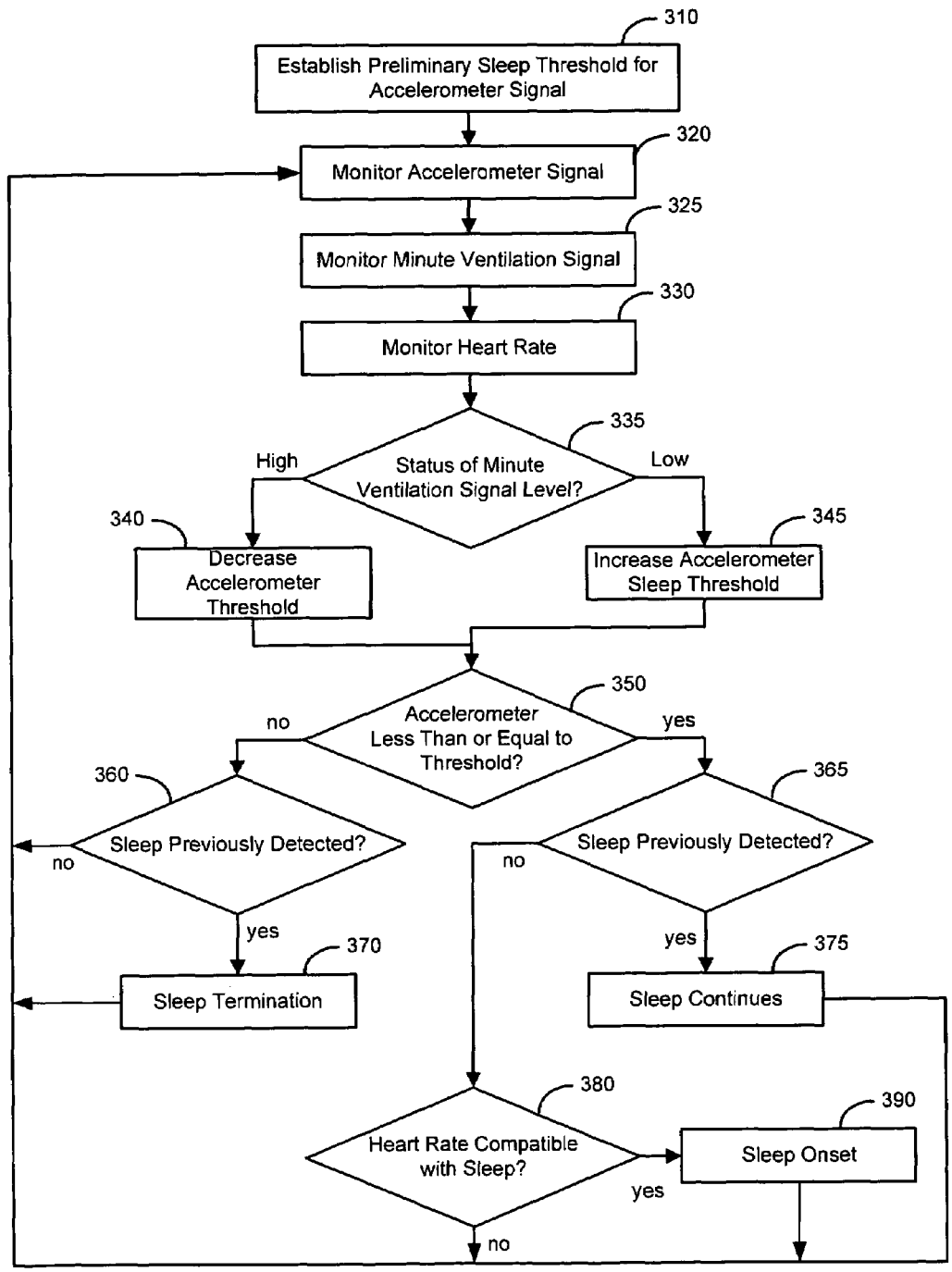
FIG. 3B is a flow chart illustrating a sleep detection method based on signals from an accelerometer and a minute ventilation sensor in accordance with embodiments of the present invention.

The flow chart illustrated in FIG. 3B is one example of an algorithmic approach to disordered breathing detection and/or prediction useful with associated detected snoring. The algorithm depicted in FIG. 3B is useful, for example, to determine a patients sleep state. In the flow chart of FIG. 3B, an accelerometer and a minute ventilation sensor are used to develop the first and second signals associated with sleep. A preliminary accelerometer signal sleep threshold is determined 310. For example, the preliminary sleep threshold may be determined from clinical data taken from a group of subjects or historical data taken from the patient over a period of time.

The activity level of the patient is monitored using an accelerometer 320 that may be incorporated into an implantable cardiac pacemaker as described above. Alternatively, the accelerometer may be attached externally to the patient. The patient's minute ventilation (MV) signal is monitored 325. The MV signal may be acquired, for example, based on the transthoracic impedance signal as described above using an implantable cardiac device. Other methods of determining the MV signal are also possible and are considered to be within the scope of this invention.

In this example, the accelerometer signal represents the sleep detection signal associated with the sleep threshold. The MV signal is the threshold adjustment signal used to adjust the sleep threshold. Heart rate is monitored 330 in this example to provide a sleep confirmation signal.

Threshold adjustment may be accomplished by using the patient's MV signal status 335 to moderate the accelerometer sleep threshold. If the patient's MV signal status 335 is low relative to an expected MV level associated with sleep, the accelerometer sleep threshold is increased. Similarly, if the patient's MV signal status 335 is high relative to an expected MV level associated with sleep, the accelerometer sleep threshold is decreased. Thus, when the patient's MV level is high, a lower level of patient activity is required to make the determination that the patient is sleeping. Conversely when the patient's MV level is relatively low, a higher patient activity level may result in detection of sleep. The use of two sleep-related signals to determine sleep enhances the accuracy of sleep detection over previous methods using only one sleep-related signal to determine that a patient is sleeping.

Various signal processing techniques may be employed to process the raw sensor signals. For example, a moving average of a plurality of samples of each sleep-related signal may be calculated and used as the sleep-related signal. Furthermore, the sleep-related signals may be filtered and/or digitized. If the MV signal status 335 is high relative to an expected MV level associated with sleep, the accelerometer sleep threshold is decreased 340. If the MV signal status 335 is low relative to an expected MV level associated with sleep, the accelerometer sleep threshold is increased 345.

If the sensed accelerometer signal is less than or equal to the adjusted sleep threshold, indicated by a yes at decision 350, and if the patient is not currently in a sleep state 365, then the patient's heart rate is checked 380 to confirm sleep. If the patient's heart rate is compatible with sleep 380, then sleep onset is determined 390. If the patient's heart rate is incompatible with sleep, then the patient's sleep-related signals continue to be monitored.

If the accelerometer signal is less than or equal to the adjusted sleep threshold at decision 350, and if the patient is currently in a sleep state 365, then a continuing sleep state 375 is determined and the patient's sleep-related signals continue to be monitored for sleep termination to occur.

If the accelerometer signal is greater than the adjusted sleep threshold, as indicated by a no condition at decision 350, and the patient is not currently in a sleep state 360, then the patient's sleep-related signals continue to be monitored until sleep onset 390 is detected. If the accelerometer signal is greater than the adjusted sleep threshold at decision 350, and the patient is currently in a sleep state 360, then sleep termination is detected 370.

The graphs of FIGS. 4-7 illustrate sensor data, trends, and the adjustment of the accelerometer sleep thresholds using the MV signal. The relationship between patient activity and the accelerometer and MV signals is trended over a period of time to determine relative signal levels associated with sleep. Adjusting and/or adapting detection and sensing levels may be helpful to determine snoring episodes during sleep, and/or to verify snoring detection based at least partly using sleep state information.

Figure 4:
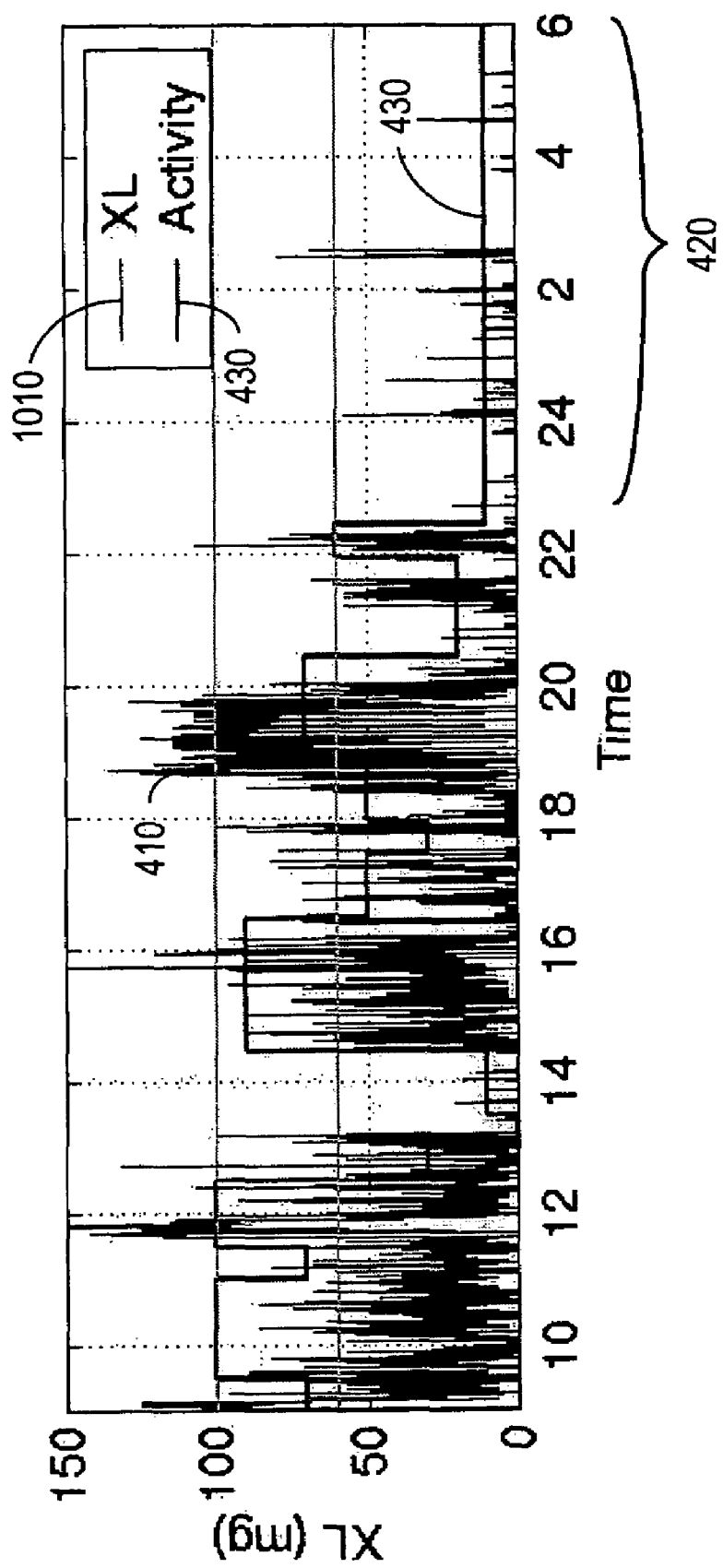
FIG. 4 is a graph of an accelerometer signal indicating patient activity level that may be used for sleep detection and therapy in accordance with embodiments of the invention.

FIG. 4 illustrates an activity level 430 as indicated by an accelerometer signal 410 (the accelerometer signal 410 is represented in the graph legend as trace XL). The accelerometer signal 410 indicates a period of sleep 420 associated with a relatively low level of activity beginning at slightly before time 23:00 and continuing through time 6:00. The accelerometer trends may be used to establish a threshold for sleep detection. The activity level 430 may be derived, for example, by integrating the accelerometer signal 410 within a moving time window, where the length of the time window is adjusted to compensate for movement during sleep or other inactivity sources or spurious activity, such as snoring episodes.

Figure 5:
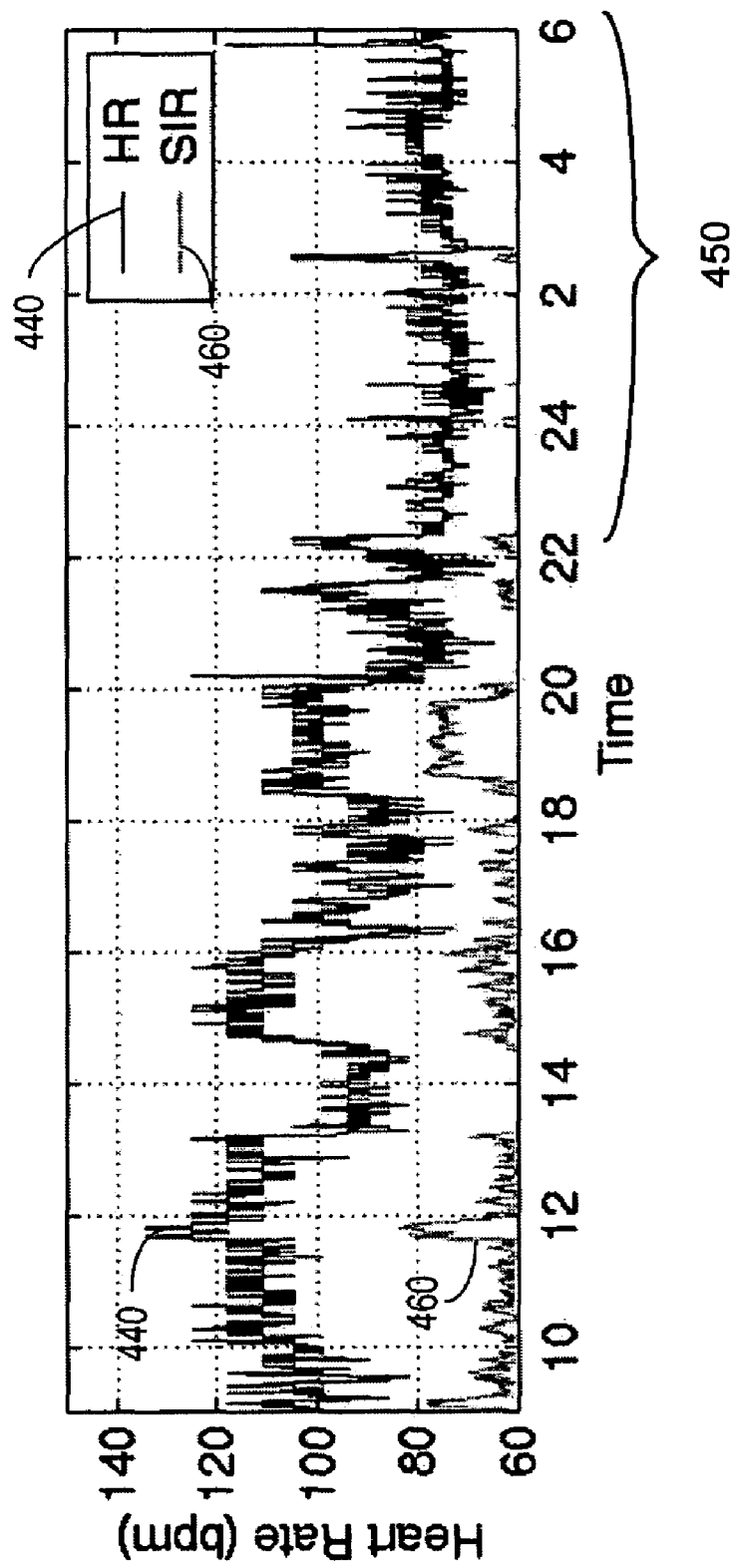
FIG. 5 is a graph of a patient's heart rate and sensor indicated rate that may be used for sleep detection and therapy in accordance with an embodiment of the invention.

The patient's heart rate for the same time period illustrated in FIG. 4 is graphed in FIG. 5. A heart rate signal 440 appropriately tracks the activity level 430 (FIG. 4) indicated by the accelerometer, indicating a similar period 450 of low heart rate corresponding to sleep. A sensor indicated rate 460 is graphed in FIG. 5, and is represented in the graph legend as trace SIR. As is illustrated in FIG. 5, the sensor indicated rate 460 may differ from the actual heart rate signal 440. For example, the sensor indicated rate 460 may be sensed from an implanted electrode or other sensor that correlates to the heart rate signal 440.

Figure 6:
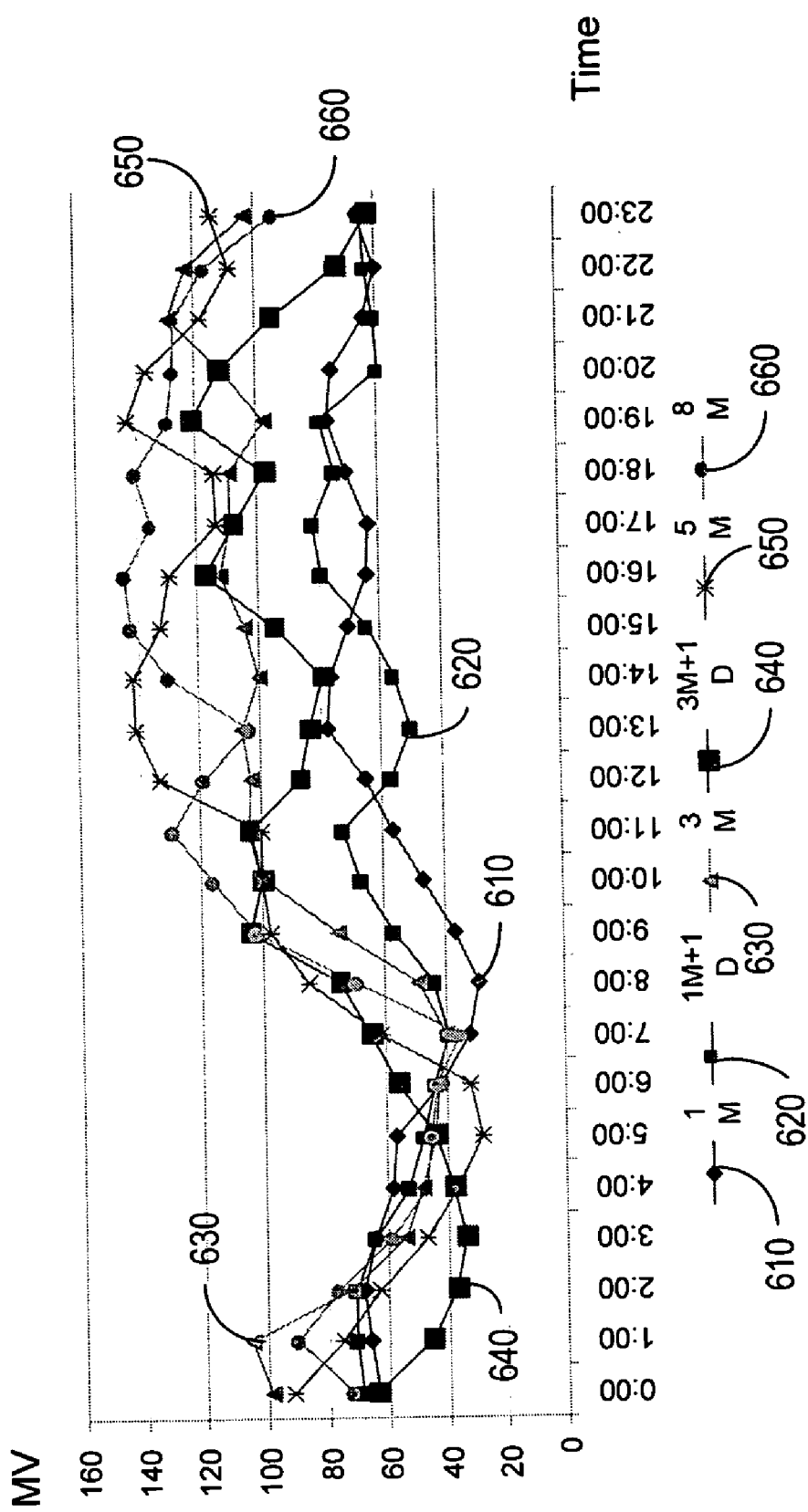
FIG. 6 is a graph of baseline trending for an MV signal used for sleep detection and therapy in accordance with embodiments of the invention.

FIG. 6 is a graph of baseline trending for an MV signal. Historical data of minute ventilation of a patient is graphed over an 8 month period. In FIG. 6, a trace is provided for: one month as a trace 610; one month plus one day as a trace 620; three months as a trace 630; three month plus one day as a trace 640; five months as a trace 650; and eight months as a trace 660. The MV signal trending data is used to determine the MV signal level associated with sleep. In this example, a composite MV signal using the historical data indicates a roughly sinusoidal shape with the relatively low MV levels occurring approximately during the period from about hours 21:00 through 8:00. The low MV levels are associated with periods of sleep, particularly evident at about hours 3:00 through 6:00 in the graphs of FIG. 6, having MV volumes from about 30 to about 60. The MV signal level associated with sleep may be used to implement sleep threshold adjustment as will be described further below and in association with FIG. 7. As described earlier, sleep threshold adjustments may be helpful to determine snoring episodes during sleep, and/or to verify snoring detection based at least partly using sleep state information.

Figure 7:
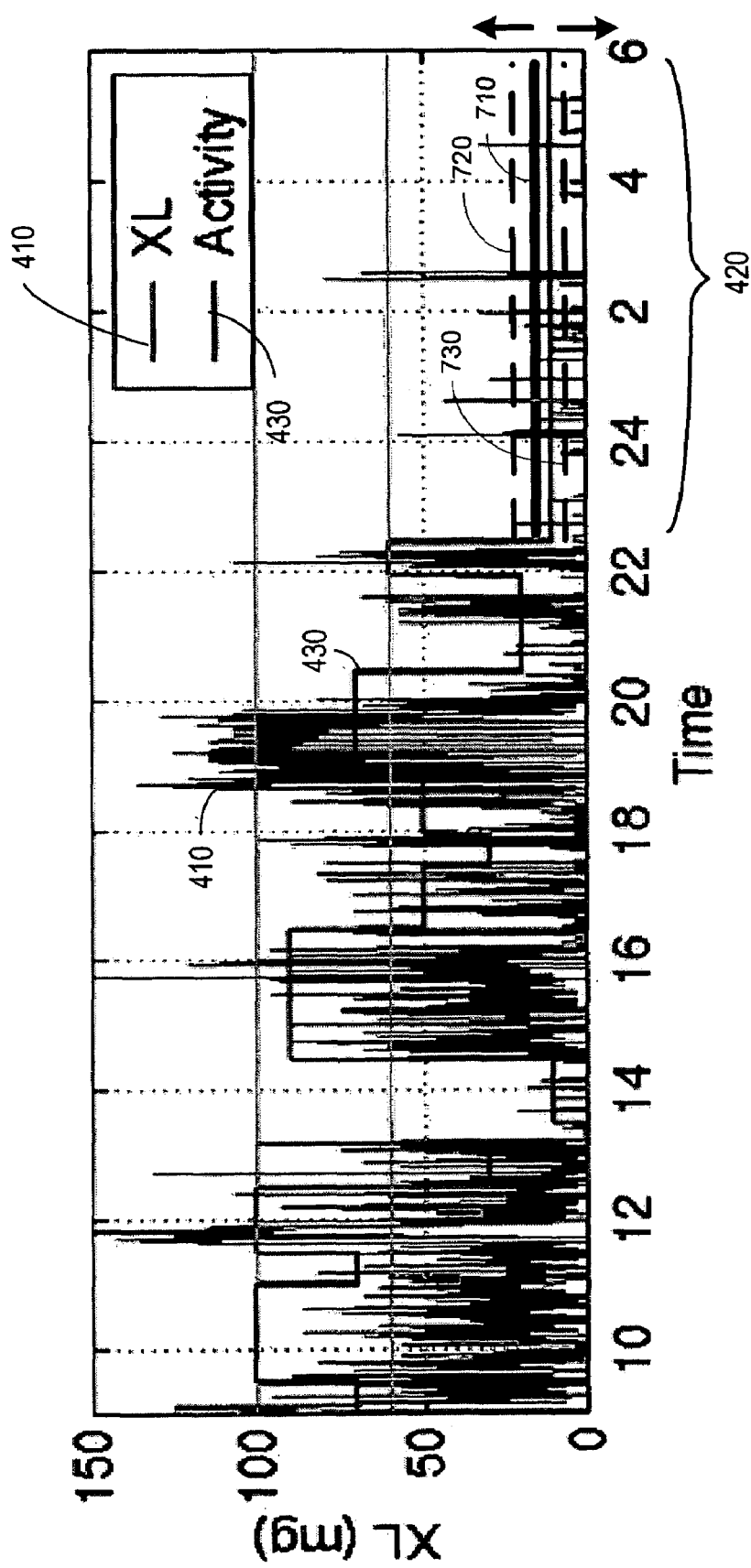
FIG. 7 illustrates adjustment of an accelerometer sleep threshold using an MV signal in accordance with embodiments of the invention

FIG. 7 illustrates adjustment of the accelerometer sleep threshold using the MV signal. FIG. 7 is based on the graph of FIG. 4, including the activity level 430 as indicated by the accelerometer signal 410 (again, represented in the graph legend as trace XL). An initial steep threshold 710 is established using the baseline accelerometer signal data acquired as discussed above. If the patient's MV signal is low relative to an expected MV level associated with sleep, the accelerometer sleep threshold is increased to an increased sleep threshold 720. If the patient's MV signal level is high relative to an expected MV level associated with sleep, the accelerometer sleep threshold is decreased to a decreased sleep threshold 730. When the patient's MV level is high, less activity detected by the accelerometer is required to make the determination that the patient is sleeping. However, if the patient's MV level is relatively low, a higher activity level may result in detection of sleep. The use of two sleep-related signals to adjust a sleep threshold for determining sleep enhances the accuracy of sleep detection.

Additional sleep-related signals may be sensed and used to improve the sleep detection mechanism described above. For example, a posture sensor may be used to detect the posture of the patient and used to confirm sleep. If the posture sensor indicates a vertical posture, then the posture sensor signal may be used to override a determination of sleep using the sleep detection and threshold adjustment signals. Other signals may also be used in connection with sleep determination or confirmation, including the representative set of sleep-related signals associated with sleep indicated above.

Various aspects of sleep quality, including number and severity of arousals, sleep disordered breathing episodes, nocturnal limb movements, and cardiac, respiratory, muscle, and nervous system functioning may provide important information for diagnosis and/or therapy delivery in addition to snoring detection. An initial step to sleep quality evaluation is an accurate and reliable method for discriminating between periods of sleep and periods of wakefulness. Further, acquiring data regarding the patient's sleep states or stages, including sleep onset, termination, REM, and NREM sleep states may be used in connection sleep quality assessment and therapy delivery. For example, the most restful sleep occurs during stages 3 and 4 NREM sleep.

One indicator of sleep quality is the percentage of time a patient spends in these sleep stages. Knowledge of the patient's sleep patterns may be used to diagnose sleep disorders and/or adjust patient therapy, including, e.g., cardiac or respiratory therapy. Trending disordered breathing episodes, arousal episodes, and other sleep quality aspects may be helpful in determining and maintaining appropriate therapies for patients suffering from disorders ranging from snoring to chronic heart failure.

As was described above, snoring may be a useful indicator, and early predictor, for disordered breathing detection and treatment. An adequate quality and quantity of sleep is required to maintain physiological homeostasis. Prolonged sleep deprivation or periods of highly fragmented sleep ultimately will have serious health consequences. Chronic lack of sleep may be associated with various cardiac or respiratory disorders affecting a patient's health and quality of life. Methods and systems for collecting and assessing sleep quality data are described in commonly owned U.S. patent application Ser. No. 10/642,998 filed on Aug. 18, 2003, now U.S. Publication No. 2005/0042589 and incorporated herein by reference in its entirety. Evaluation of the patient's sleep patterns and sleep quality may be an important aspect of providing coordinated therapy to the patient, including respiratory and cardiac therapy.

Figure 8:
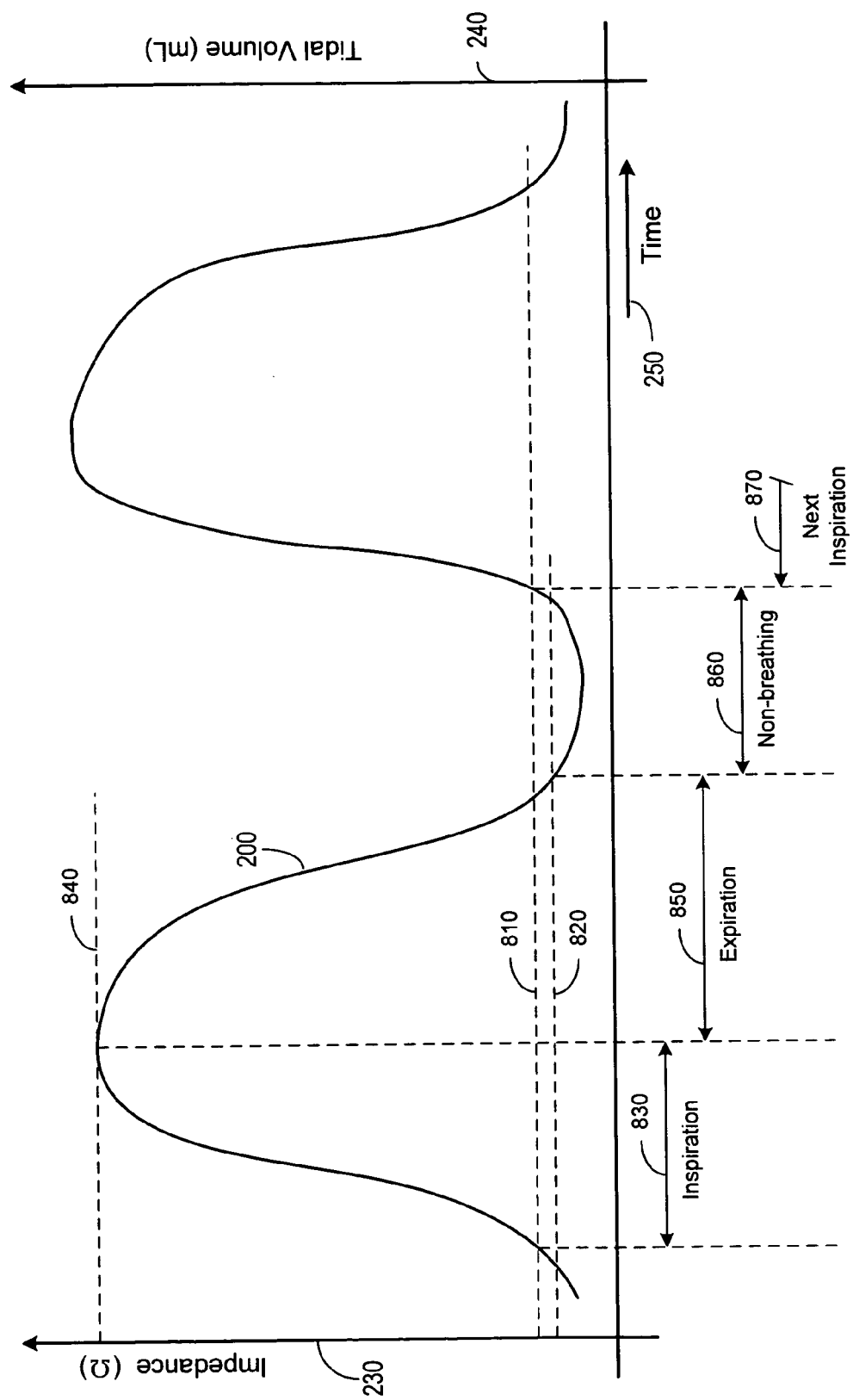
FIG. 8 is a respiration signal graph illustrating respiration intervals used for disordered breathing detection and/or prediction according to embodiments of the invention.
Figure 9:
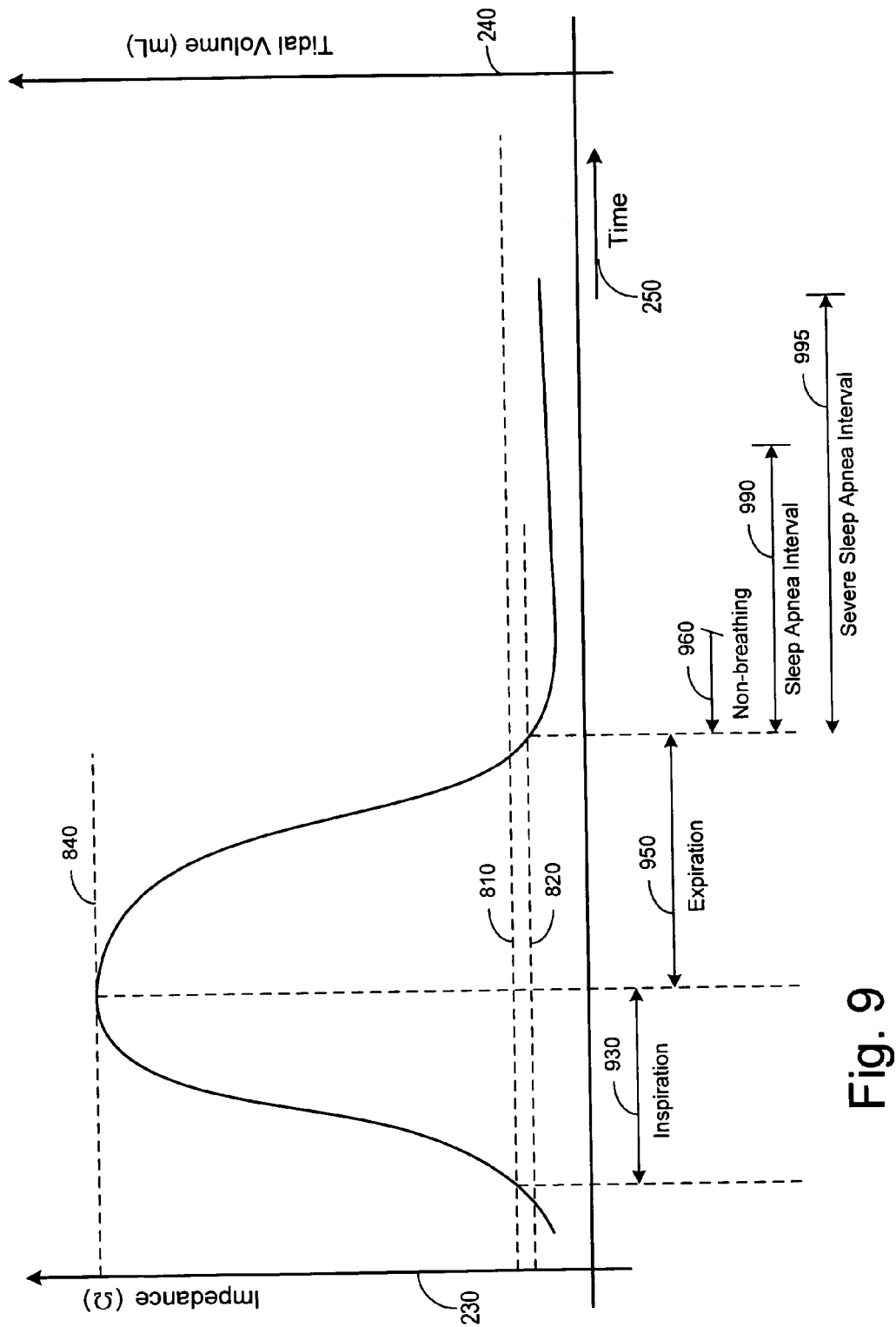
FIG. 9 is a graph of a respiration signal illustrating various intervals that may be used for detection of apnea in accordance with embodiments of the invention.
Figure 10:
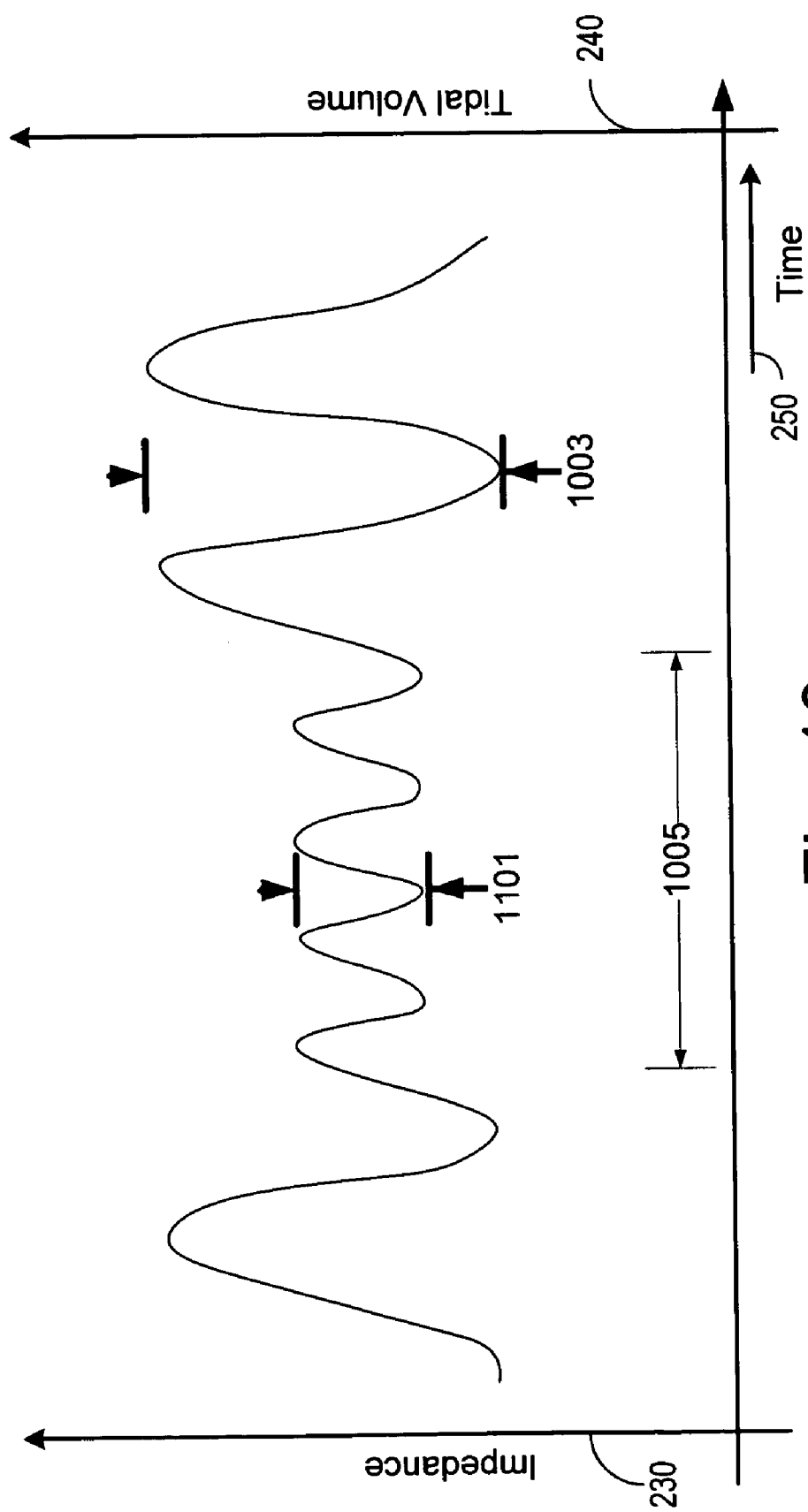
FIG. 10 is a respiration graph illustrating abnormally shallow respiration utilized in detection of disordered breathing in accordance with embodiments of the invention.

Snoring and disordered breathing occur during sleep, and detecting and discriminating between episodes and types of breathing may be useful for proper treatment of detected disorders. FIGS. 8-10 are graphs of transthoracic impedance and tidal volume, similar to FIG. 2 previously described. As in FIG. 2, FIGS. 8-10 illustrate the impedance signal 200 proportional to the transthoracic impedance, again illustrated as Impedance 230 on the abscissa of the left side of the graphs in FIGS. 8-10. The impedance 230 increases during any respiratory inspiration 220 and decreases during any respiratory expiration 210. As before, the impedance signal 200 is also proportional to the amount of air inhaled, denoted the tidal volume 240, illustrated on the abscissa of the right side of the graph in FIGS. 8-10. The magnitude of variations in impedance and tidal volume during respiration are identifiable as the peak-to-peak variation of the impedance signal 200.

FIG. 8 illustrates respiration intervals used for disordered breathing detection and/or prediction useful in accordance with embodiments of the present invention. Detection of disordered breathing may involve defining and examining a number of respiratory cycle intervals. A respiration cycle is divided into an inspiration period corresponding to the patient inhaling, an expiration period, corresponding to the patient exhaling, and a non-breathing period occurring between inhaling and exhaling. Respiration intervals are established using an inspiration threshold 810 and an expiration threshold 820. The inspiration threshold 810 marks the beginning of an inspiration period 830 and is determined by the transthoracic impedance signal 700 rising above the inspiration threshold 810. The inspiration period 830 ends when the transthoracic impedance signal 200 is a maximum 840. The maximum transthoracic impedance signal 840 corresponds to both the end of the inspiration interval 830 and the beginning of an expiration interval 850. The expiration interval 850 continues until the transthoracic impedance 200 falls below an expiration threshold 820. A non-breathing interval 860 starts from the end of the expiration period 850 and continues until the beginning of a next inspiration period 870.

Detection of sleep apnea and severe sleep apnea is illustrated in FIG. 9. The patient's respiration signals are monitored and the respiration cycles are defined according to an inspiration 930, an expiration 950, and a non-breathing 960 interval as described in connection with FIG. 8. Sleep apnea is detected when a non-breathing period 960 exceeds a first predetermined interval 990, denoted the sleep apnea interval. Severe sleep apnea is detected when the non-breathing period 960 exceeds a second predetermined interval 995, denoted the severe sleep apnea interval. For example, sleep apnea may be detected when the non-breathing interval exceeds about 10 seconds, and severe sleep apnea may be detected when the non-breathing interval exceeds about 20 seconds.

Hypopnea is a form of disordered breathing characterized by abnormally shallow breathing. FIG. 10 is a graph of tidal volume derived from transthoracic impedance measurements. The graph of FIG. 10 illustrating the tidal volume of a hypopnea episode may be compared to the tidal volume of a normal breathing cycle illustrated previously in FIG. 2, which illustrated normal respiration tidal volume and rate. As shown in FIG. 10, hypopnea involves a period of abnormally shallow respiration, possible at an increased respiration rate.

Hypopnea is detected by comparing a patient's respiratory tidal volume 1003 to a hypopnea tidal volume 1001. The tidal volume for each respiration cycle may be derived from transthoracic impedance measurements acquired in the manner described previously. The hypopnea tidal volume threshold may be established by, for example, using clinical results providing a representative tidal volume and duration of hypopnea events. In one configuration, hypopnea is detected when an average of the patient's respiratory tidal volume taken over a selected time interval falls below the hypopnea tidal volume threshold. Furthermore, various combinations of hypopnea cycles, breath intervals, and non-breathing intervals may be used to detect hypopnea, where the non-breathing intervals are determined as described above.

In FIG. 10, a hypopnea episode 1005 is identified when the average tidal volume is significantly below the normal tidal volume. In the example illustrated in FIG. 10, the normal tidal volume during the breathing process is identified as the peak-to peak value identified as the respiratory tidal volume 1003. The hypopnea tidal volume during the hypopnea episode 1005 is identified as hypopnea tidal volume 1001. For example, the hypopnea tidal volume 1001 may be about 50% of the respiratory tidal volume 1003. The value 50% is used by way of example only, and determination of thresholds for hypopnea events may be determined as any value appropriate for a given patient. In the example above, if the tidal volume falls below 50% of the respiratory tidal volume 1003, the breathing episode may be identified as a hypopnea event, originating the measurement of the hypopnea episode 1005.

Figure 11:
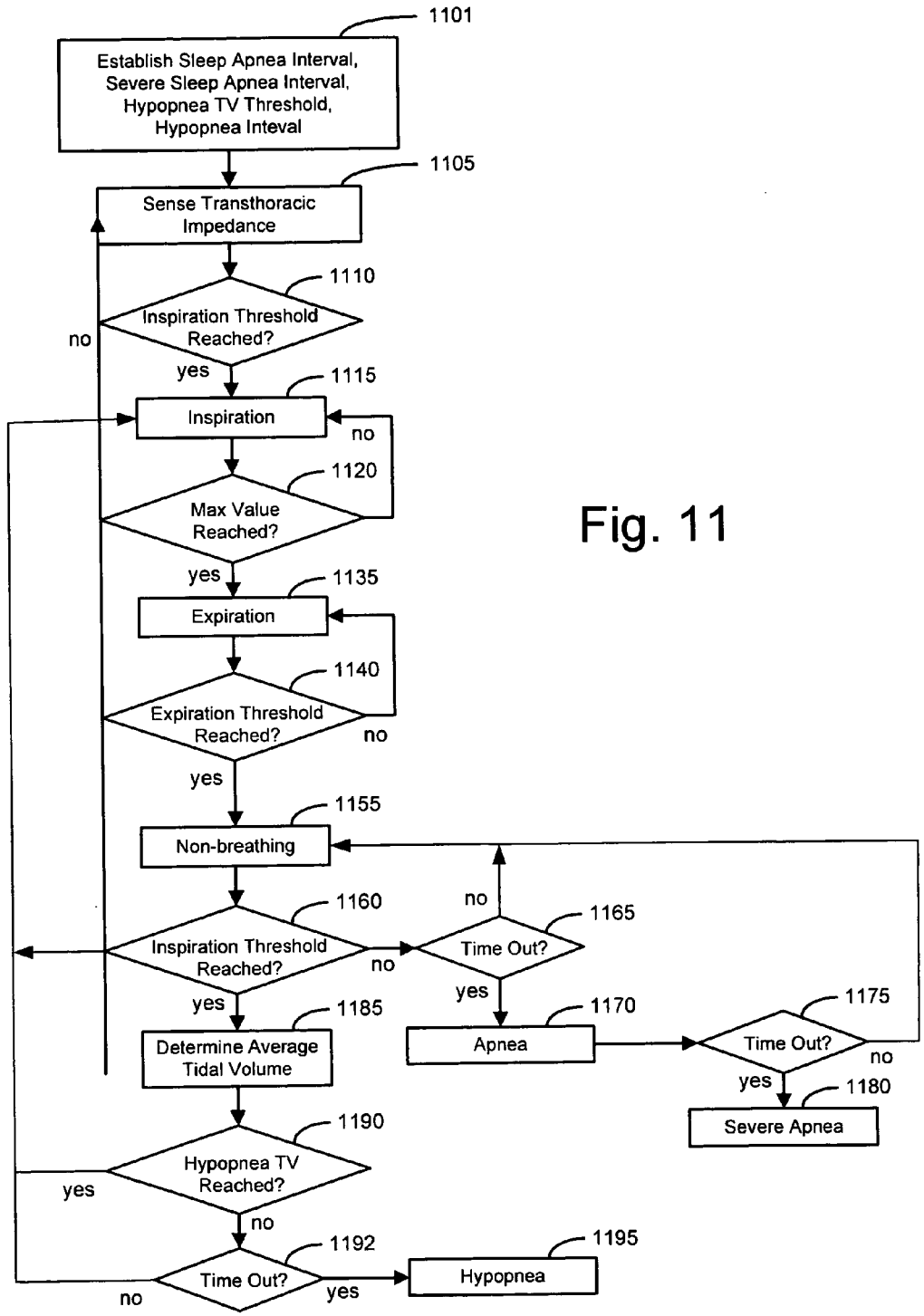
FIG. 11 is a flow chart illustrating a method of apnea and/or hypopnea detection according to embodiments of the invention.

FIG. 11 is a flow chart illustrating a method of apnea and/or hypopnea detection useful in accordance with embodiments of the present invention. Various parameters are established 1101 before analyzing the patient's respiration for disordered breathing episodes, including, for example, inspiration and expiration thresholds, sleep apnea interval, severe sleep apnea interval, and hypopnea tidal volume (TV) threshold.

The patient's transthoracic impedance is measured 1105 as described in more detail above. If the transthoracic impedance exceeds 1110 the inspiration threshold, the beginning of an inspiration interval is detected 1115. If the transthoracic impedance remains below 1110 the inspiration threshold, then the impedance signal is checked 1105 periodically until inspiration 1115 occurs.

During the inspiration interval, the patient's transthoracic impedance is monitored until a maximum value of the transthoracic impedance is detected 1120. Detection of the maximum value signals an end of the inspiration period and a beginning of an expiration period 1135.

The expiration interval is characterized by decreasing transthoracic impedance. When, at determination 1140, the transthoracic impedance falls below the expiration threshold, a non-breathing interval is detected 1155.

If the transthoracic impedance determination 1160 does not exceed the inspiration threshold within a first predetermined interval, denoted the sleep apnea interval 1165, then sleep apnea is detected 1170. Severe sleep apnea 1180 is detected if the non-breathing period extends beyond a second predetermined interval, denoted the severe sleep apnea interval 1175.

When the transthoracic impedance determination 1160 exceeds the inspiration threshold, the tidal volume from the peak-to-peak transthoracic impedance is calculated, along with a moving average of past tidal volumes 1185. The peak-to-peak transthoracic impedance provides a value proportional to the tidal volume of the respiration cycle. This value is compared at determination 1190 to a hypopnea tidal volume threshold. If, at determination 1190, the peak-to-peak transthoracic impedance is consistent with the hypopnea tidal volume threshold for a predetermined time 1192, then a hypopnea cycle 1195 is detected.

Cardiac stimulation may also be used as a therapy for disordered breathing, and may be combined with CPAP therapy and/or snoring detection systems and methods in accordance with embodiments of the present invention. Therapy methods for disordered breathing based on cardiac electrical stimulation are described in commonly owned U.S. patent application Ser. No. 10/643,203 filed on Aug. 18, 2003, now U.S. Publication No. 2005/0039745 and U.S. patent application Ser. No. 10/643,154 filed on Aug. 18, 2003, now U.S. Publication No. 2005/0043772 both of which are incorporated by reference herein. Disordered breathing detection and prediction systems and methods are further described in U.S. patent application Ser. No. 10/309,771 filed Dec. 4, 2002, now U.S. Pat. No. 7,189,204; Ser. No. 10/309,770 filed Dec. 4, 2002, now U.S. Pat. No. 7,252,640; and Ser. No. 10/643,016 filed Aug. 18, 2003, now U.S. Pat. No. 7,396,333 all of which are hereby incorporated by reference herein.

Figure 12:
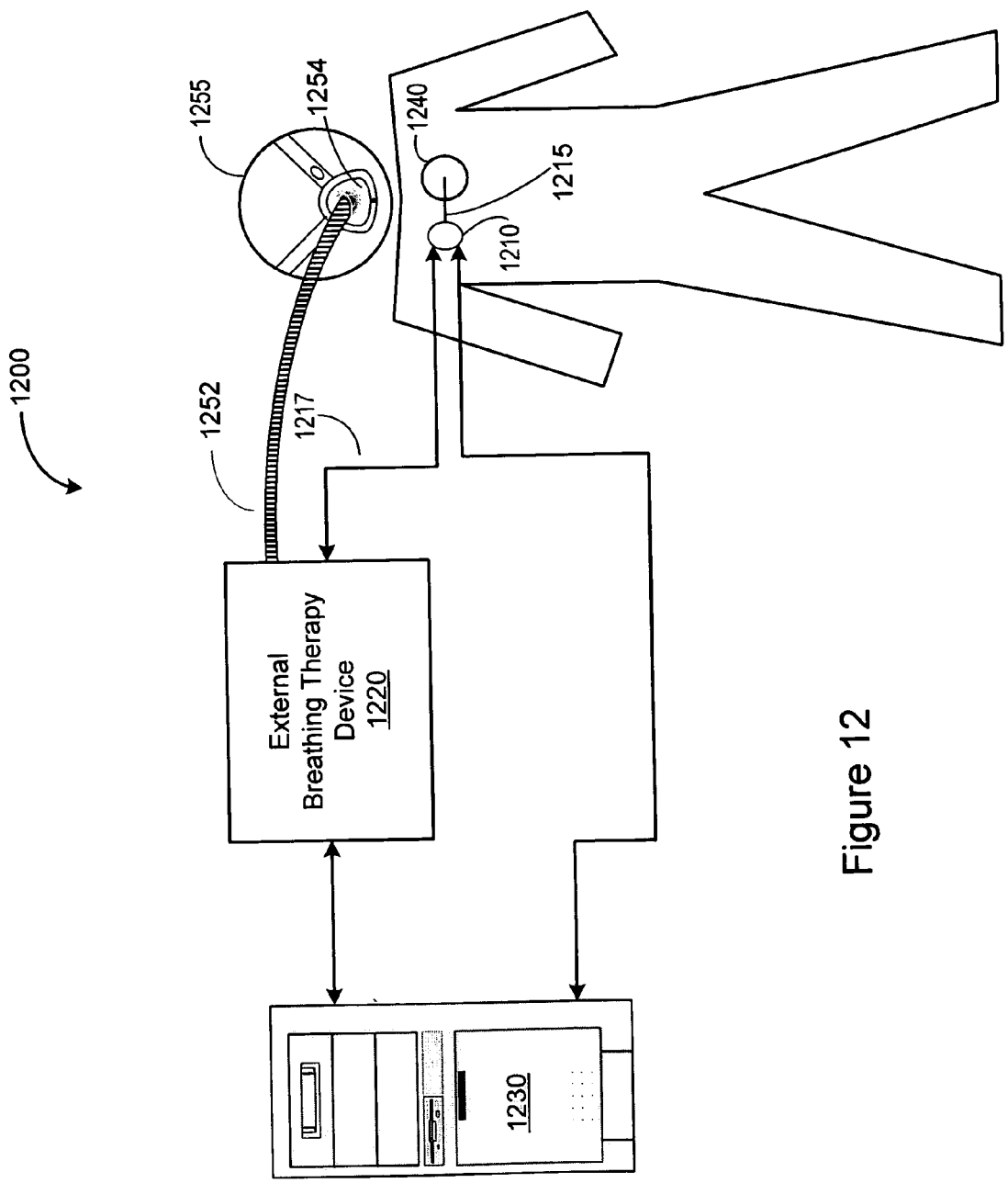
FIG. 12 illustrates a medical system including an implantable cardiac rhythm management device that cooperates with a patient-external respiration therapy device to provide coordinated patient monitoring, diagnosis and/or therapy in accordance with an embodiment of the present invention.

According to one embodiment of the present invention, illustrated in FIG. 12, a medical system 1200 may include an implantable cardiac rhythm management device 1210 that cooperates with a patient-external respiration therapy device 1220 to provide coordinated patient monitoring, diagnosis and/or therapy. In this configuration, the implantable cardiac rhythm management device (CRM) 1210 operates as the patient-internal medical device 110 described with reference to FIG. 16. The CRM 1210 may provide a first set of monitoring, diagnostic, and/or therapeutic functions to a patient 1255. The CRM 1210 may be electrically coupled to a patient's heart 1240 through one or more cardiac electrodes 1215 terminating in, on, or about the heart 1240. The cardiac electrodes 1215 may sense cardiac signals produced by the heart 1240 and/or provide therapy to one or more heart chambers. For example, the cardiac electrodes 1215 may deliver electrical stimulation to one or more heart 1240 chambers, and/or to one or multiple sites within the heart 1240 chambers. The CRM 1210 may directly control delivery of one or more cardiac therapies, such as cardiac pacing, defibrillation, cardioversion, cardiac resynchronization, and/or other cardiac therapies, for example. In addition, the CRM 1210 may facilitate the control of a mechanical respiration device 1220. Further, the CRM 1210 may perform various monitoring and/or diagnostic functions in relation to the cardiovascular system and/or other physiological systems.

In the example illustrated in FIG. 12, a mechanical respiration therapy CPAP device 1220 comprises a positive airway pressure device that cooperates with a CRM 1210. The CPAP device 1220 develops a positive air pressure that is delivered to the patient's airway through a tube system 1252 and a mask 1254 connected to the CPAP device 1220. Positive airway pressure devices are often used to treat snoring and disordered breathing. In one configuration, for example, the positive airway pressure provided by the CPAP device 1220 acts as a pneumatic splint keeping the patient's airway open and reducing the severity and/or number of occurrences of disordered breathing and/or snoring due to airway obstruction.

The CPAP device 1220 may directly control the delivery of respiration therapy to the patient, and may contribute to the control of the CRM device 1210. In addition, the CPAP device 1220 may provide a number of monitoring and/or diagnostic functions in relation to the respiratory system and/or other physiological systems.

The CRM 1210 and CPAP 1220 devices may communicate directly through a wireless communications link 1217, for example. Alternatively, or additionally, the CRM 1210 and CPAP 1220 devices may communicate with and/or through an APM such as the APM system 1230, as will be described further below with reference to FIG. 16.

Although FIG. 12 illustrates a CRM device 1210 used with a CPAP device 1220 to provide coordinated patient monitoring, diagnosis and/or therapy, any number of patient-internal and patient-external medical devices may be included in a medical system in accordance with the present invention. For example, a drug delivery device, such as a drug pump or controllable nebulizer, may be included in the system 1200. The drug delivery device may cooperate with either or both of the CRM device 1210 and the CPAP device 1220 and may contribute to the patient monitoring, diagnosis, and/or therapeutic functions of the medical system 1200.

Figure 13:
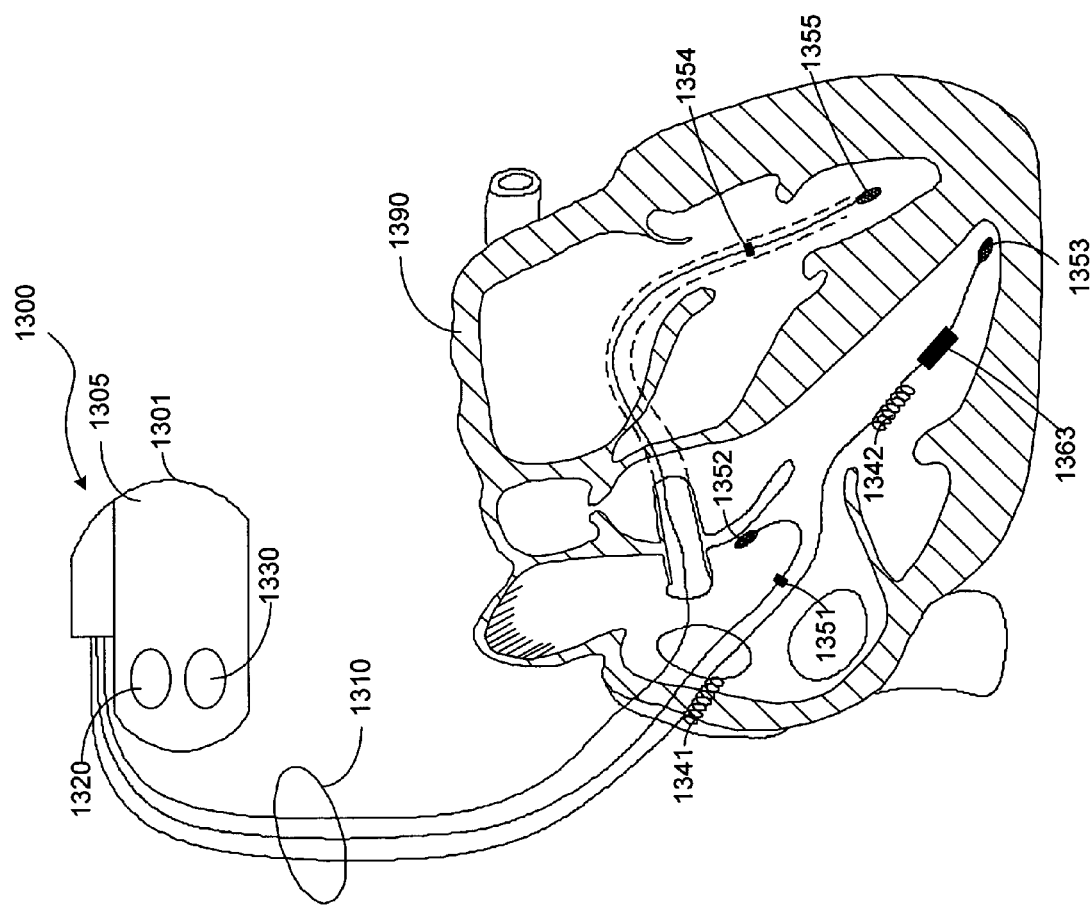
FIG. 13 is an illustration of an implantable cardiac device including a lead assembly shown implanted in a sectional view of a heart, the device used for coordinated patient monitoring, diagnosis, and/or therapy in accordance with embodiments of the present invention.

Referring now to FIG. 13, the implantable device illustrated in FIG. 13 is an embodiment of a PIMD that may benefit from snoring detection in accordance with the present invention. In this example, the implantable device includes a cardiac rhythm management device (CRM) 1300 including an implantable pulse generator 1305 electrically and physically coupled to an intracardiac lead system 1310.

Portions of the intracardiac lead system 1310 are inserted into the patient's heart 1390. The intracardiac lead system 1310 includes one or more electrodes configured to sense electrical cardiac activity of the heart, deliver electrical stimulation to the heart, sense the patient's transthoracic impedance, and/or sense other physiological parameters, e.g., cardiac chamber pressure or temperature. Portions of the housing 1301 of the pulse generator 1305 may optionally serve as a can electrode.

Communications circuitry is disposed within the housing 1301 for facilitating communication between the pulse generator 1305 and an external communication device, such as a portable or bed-side communication station, patient-carried/worn communication station, or external programmer, for example. The communications circuitry may also facilitate unidirectional or bidirectional communication with one or more implanted, external, cutaneous, or subcutaneous physiologic or non-physiologic sensors, patient-input devices and/or information systems.

The pulse generator 1305 may optionally incorporate a motion detector 1320 that may be used to sense various respiration-related conditions. For example, the motion detector 1320 may be optionally configured to sense snoring, activity level, and/or chest wall movements associated with respiratory effort, for example. The motion detector 1320 may be implemented as an accelerometer positioned in or on the housing 1301 of the pulse generator 1305. If the motion sensor is implemented as an accelerometer, the motion sensor may also provide respiratory, e.g. rales, coughing, and cardiac, e.g. S1-S4 heart sounds, murmurs, and other acoustic information.

The lead system 1310 of the CRM 1300 may incorporate one or more transthoracic impedance sensors that may be used to acquire the patient's respiration waveform, or other respiration-related information. The transthoracic impedance sensor may include, for example, one or more intracardiac electrodes 1341, 1342, 1351-1355, 1363 positioned in one or more chambers of the heart 1390. The intracardiac electrodes 1341, 1342, 1351-1355, 1363 may be coupled to impedance drive/sense circuitry 1330 positioned within the housing of the pulse generator 1305.

In one implementation, impedance drive/sense circuitry 1330 generates a current that flows through the tissue between an impedance drive electrode 1351 and a can electrode on the housing 1301 of the pulse generator 1305. The voltage at an impedance sense electrode 1352 relative to the can electrode changes as the patient's transthoracic impedance changes. The voltage signal developed between the impedance sense electrode 1352 and the can electrode is detected by the impedance sense circuitry 1330. Other locations and/or combinations of impedance sense and drive electrodes are also possible.

The lead system 1310 may include one or more cardiac pace/sense electrodes 1351-1355 positioned in, on, or about one or more heart chambers for sensing electrical signals from the patient's heart 1390 and/or delivering pacing pulses to the heart 1390. The intracardiac sense/pace electrodes 1351-1355, such as those illustrated in FIG. 13, may be used to sense and/or pace one or more chambers of the heart, including the left ventricle, the right ventricle, the left atrium and/or the right atrium. The lead system 1310 may include one or more defibrillation electrodes 1341, 1342 for delivering defibrillation/cardioversion shocks to the heart.

The pulse generator 1305 may include circuitry for detecting cardiac arrhythmias and/or for controlling pacing or defibrillation therapy in the form of electrical stimulation pulses or shocks delivered to the heart through the lead system 1310. The pulse generator 1305 may also incorporate circuitry, structures and functionality of the implantable medical devices disclosed in commonly owned U.S. Pat. Nos. 5,203,348; 5,230,337; 5,360,442; 5,366,496; 5,397,342; 5,391,200; 5,545,202; 5,603,732; and 5,916,243, which are hereby incorporated herein by reference.

Figure 14:
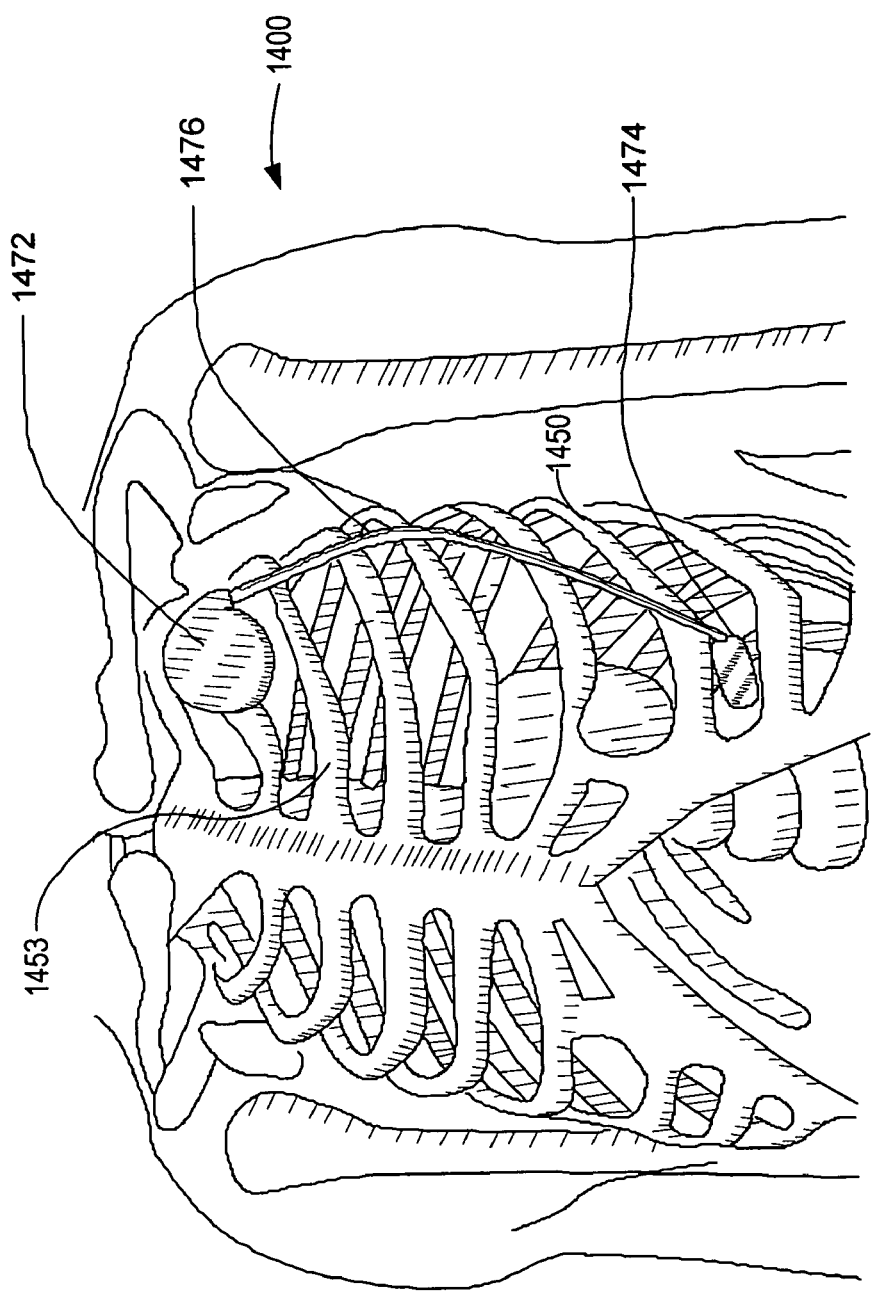
FIG. 14 is an illustration of a thorax having an implanted subcutaneous medical device that may be used for coordinated patient monitoring, diagnosis, and/or therapy in accordance with an embodiment of the present invention.

FIG. 14 is a diagram illustrating a subcutaneous implantable medical device 1400 that may be used for detecting snoring and determining the presence of sleep disordered breathing in accordance with embodiments of the present invention. The device 1400 illustrated in FIG. 14 is an implantable transthoracic cardiac sensing and/or stimulation (ITCS) device that may be implanted under the skin in the chest region of a patient. The ITCS device may, for example, be implanted subcutaneously such that all or selected elements of the device are positioned on the patient's front, back, side, or other body locations suitable for sensing cardiac activity and delivering cardiac stimulation therapy. It is understood that elements of the ITCS device may be located at several different body locations, such as in the chest, abdominal, or subclavian region with electrode elements respectively positioned at different regions near, around, in, or on the heart.

The primary housing (e.g., the active or non-active can) of the ITCS device, for example, may be configured for positioning outside of a rib cage 1450 at an intercostal or subcostal location, within the abdomen, or in the upper chest region (e.g., subclavian location, such as above a third rib 1453). In one implementation, one or more electrodes may be located on a primary housing 1472 and/or at other locations about, but not in direct contact with the heart, great vessel or coronary vasculature.

Communications circuitry may be disposed within the housing 1472 for facilitating communication between the ITCS device and an external communication device, such as a portable or bed-side communication station, patient-carried/worn communication station, or external programmer, for example. The communications circuitry may also facilitate unidirectional or bidirectional communication with one or more external, cutaneous, or subcutaneous physiologic or non-physiologic sensors. The housing 1472 is typically configured to include one or more electrodes (e.g., can electrode and/or indifferent electrode). Although the housing 1472 is typically configured as an active can, it is appreciated that a non-active can configuration may be implemented, in which case at least two electrodes spaced apart from the housing 1472 are employed.

In the configuration shown in FIG. 14, a subcutaneous electrode 1474 may be positioned under the skin in the chest region and situated distal from the housing 1472. The subcutaneous and, if applicable, housing electrode(s) may be positioned about the heart at various locations and orientations, such as at various anterior and/or posterior locations relative to the heart. The subcutaneous electrode 1474 is coupled to circuitry within the housing 1472 via a lead assembly 1476. One or more conductors (e.g., coils or cables) are provided within the lead assembly 1476 and electrically couple the subcutaneous electrode 1474 with circuitry in the housing 1472. One or more sense, sense/pace or defibrillation electrodes may be situated on the elongated structure of the electrode support, the housing 1472, and/or the distal electrode assembly (shown as subcutaneous electrode 1474 in the configuration shown in FIG. 14).

In one configuration, the electrode support assembly and the housing 1472 define a unitary structure (e.g., a single housing/unit). The electronic components and electrode conductors/connectors are disposed within or on the unitary ITCS device housing/electrode support assembly. At least two electrodes are supported on the unitary structure near opposing ends of the housing/electrode support assembly. The unitary structure may have an arcuate or angled shape, for example.

According to another configuration, the electrode support assembly defines a physically separable unit relative to the housing 1472. The electrode support assembly includes mechanical and electrical couplings that facilitate mating engagement with corresponding mechanical and electrical couplings of the housing 1472. For example, a header block arrangement may be configured to include both electrical and mechanical couplings that provide for mechanical and electrical connections between the electrode support assembly and housing 1472. The header block arrangement may be provided on the housing 1472 or the electrode support assembly. Alternatively, a mechanical/electrical coupler may be used to establish mechanical and electrical connections between the electrode support assembly and housing 1472. In such a configuration, a variety of different electrode support assemblies of varying shapes, sizes, and electrode configurations may be made available for physically and electrically connecting to a standard ITCS device housing 1472.

Various embodiments described herein may be used in connection with subcutaneous monitoring, diagnosis, and/or therapy. Methods, structures, and/or techniques described herein relating to subcutaneous systems and methods may incorporate features of one or more of the following references: commonly owned U.S. patent applications: Ser. No. 60/462,272, filed Apr. 11, 2003; Ser. No. 10/462,001, filed Jun. 13, 2003, now U.S. Publication No. 2004/0230229; Ser. No. 10/465,520, filed Jun. 19, 20003, now U.S. Publication No. 2004/0230230; Ser. No. 10/820,642, filed Apr. 8, 2004, now U.S. Publication No. 2004/0215258; and Ser. No. 10/821,248, filed Apr. 8, 2004, now U.S. Publication No. 2004/0215240, each hereby incorporated herein by reference.

Figure 15:
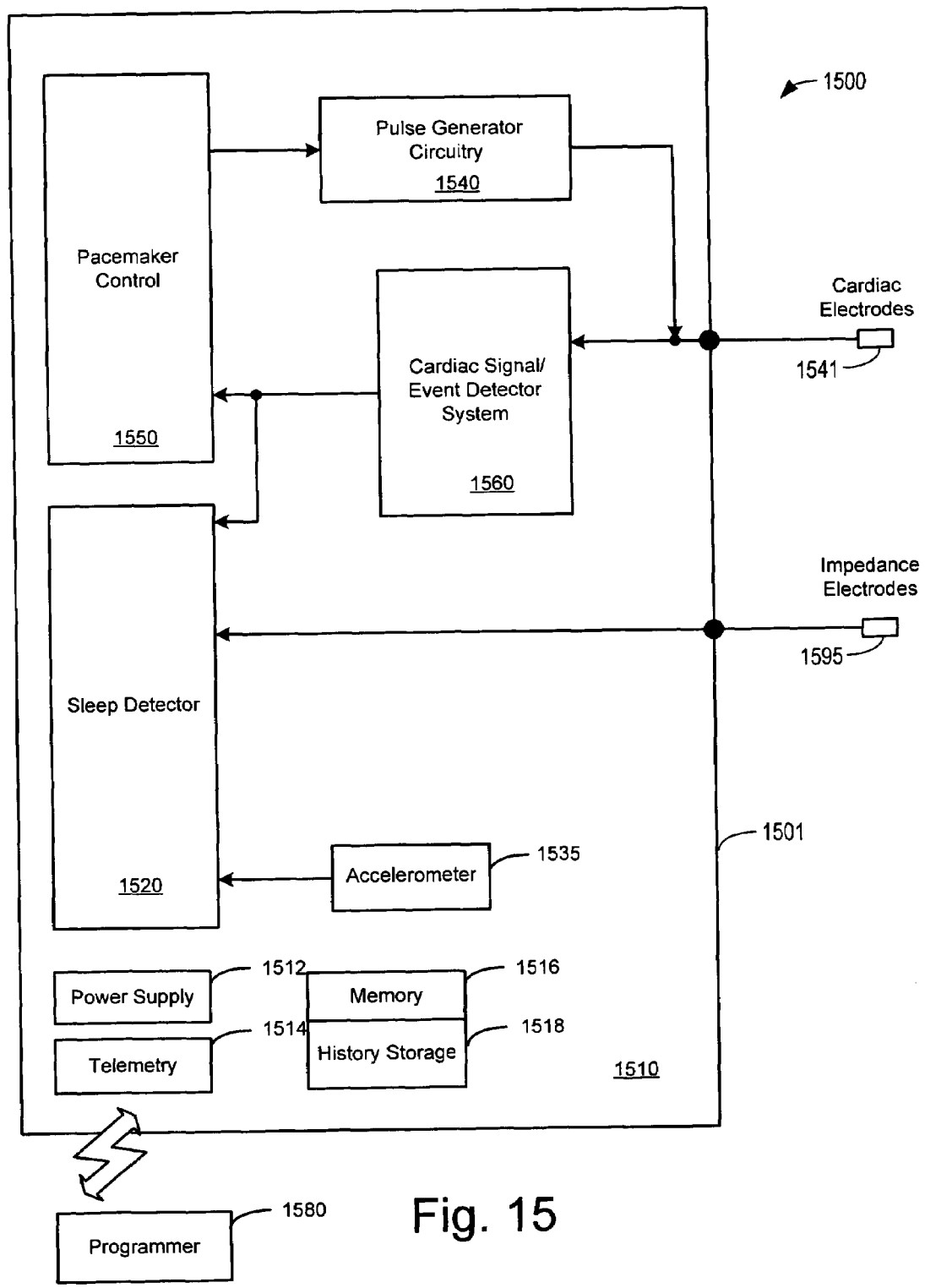
FIG. 15 is a block diagram of a cardiac rhythm management (CRM) system configured as a pacemaker and suitable for implementing a sleep and snoring detection methodology in accordance with embodiments of the present invention.

Referring now to FIG. 15, there is shown a block diagram of an embodiment of a CRM system 1500 configured as a pacemaker and suitable for implantably detecting snoring and determining the presence of sleep disordered breathing in accordance with the present invention. FIG. 15 shows the CRM 1500 divided into functional blocks. The CRM 1500 includes a sleep detector 1520 for receiving sleep-related signals and detecting sleep in accordance with embodiments of the invention.

In one embodiment, the sleep detector 1520 is incorporated as part of CRM circuitry 1510 encased and hermetically sealed in a housing 1501 suitable for implanting in a human body. Power to the CRM 1500 is supplied by an electrochemical battery power supply 1512 housed within the CRM 1500. A connector block (not shown) is additionally attached to the CRM 1500 to allow for the physical and electrical attachment of the cardiac lead system conductors to the CRM circuitry 1510.

The CRM circuitry 1510 may be configured as a programmable microprocessor-based system, with circuitry for detecting sleep in addition to providing pacing therapy to the heart. Cardiac signals sensed by one or more cardiac electrodes 1541 may be processed by the cardiac event detection circuitry 1560. Pace pulses controlled by the pacemaker control 1550 and generated by the pulse generator 1540 are delivered to the heart to treat various arrhythmias of the heart.

The memory circuit 1516 may store parameters for various device operations involved in sleep detection and/or cardiac pacing and sensing. The memory circuit 1516 may also store data indicative of snoring and other sleep-related signals received by components of the CRM circuitry 1510, such as information derived from one or more impedance electrodes 1595, the cardiac signal detector system 1560, the accelerometer 1535, and/or the sleep detector 1520.

As is illustrated in FIG. 15, the sleep detector 1520 receives signals derived from the cardiac event detector 1560, the impedance electrodes 1595 and the accelerometer 1535 to perform operations involving detecting snoring, sleep onset, arousal, and sleep termination, for example. Historical data storage 1518 may be coupled to the sleep detection circuitry 1520 for storing historical snoring data and/or other sleep related data. Such data may be transmitted to an external programmer unit 1580 and used for various diagnostic purposes and as needed or desired.

Telemetry circuitry 1514 is coupled to the CRM circuitry 1510 to allow the CRM 1500 to communicate with a remote device such as the programmer 1580, or other device. In one embodiment, the telemetry circuitry 1514 and the programmer 1580 use a wire loop antenna and a radio frequency telemetric link to receive and transmit signals and data between the programmer 1580 and telemetry circuitry 1514. In this manner, programming commands and data may be transferred between the CRM circuitry 1510 and the one or more remote devices 1580 during and after implant.

The programming commands allow a physician to set or modify various parameters used by the CRM system 1500. These parameters may include setting sleep detection parameters for use during sleep detection, such as which sleep-related signals are to be used for sleep detection and threshold adjustment, and the initial sleep detection thresholds. In addition, the CRM system 1500 may download to the programmer 1580 stored data pertaining to sensed sleep periods, including the amount of time spent sleeping, the time of day sleep periods occurred, historical data of sleep times, and the number of arousals during the sleep periods, for example.

Still referring to FIG. 15, signals associated with patient activity may be detected through the use of an accelerometer 1535 positioned within the housing 1501 of the CRM 1500. The accelerometer 1535 may be responsive to patient activity and/or motion such as from snoring, movement, and/or other activity. The accelerometer signal may be correlated with activity level or workload, for example. Signals derived from the accelerometer 1535 are coupled to the sleep detector 1520 and may also be used by the pacemaker 1550 for implementing a rate adaptive pacing regimen, for example, as well as implementing snoring detection in accordance with the present invention.

The impedance electrodes 1595 sense the patient's transthoracic impedance. The transthoracic impedance may be used to calculate various parameters associated with respiration, including snoring for example. Impedance driver circuitry (not shown) induces a current that flows through the blood between the impedance drive electrode and a can electrode on the housing 1501 of the CRM 1500. The voltage at an impedance sense electrode relative to the can electrode changes as the transthoracic impedance changes. The voltage signal developed between the impedance sense electrode and the can electrode is detected by the impedance sense amplifier and is delivered to the sleep detector circuitry 1520 for further processing.

Figure 16:
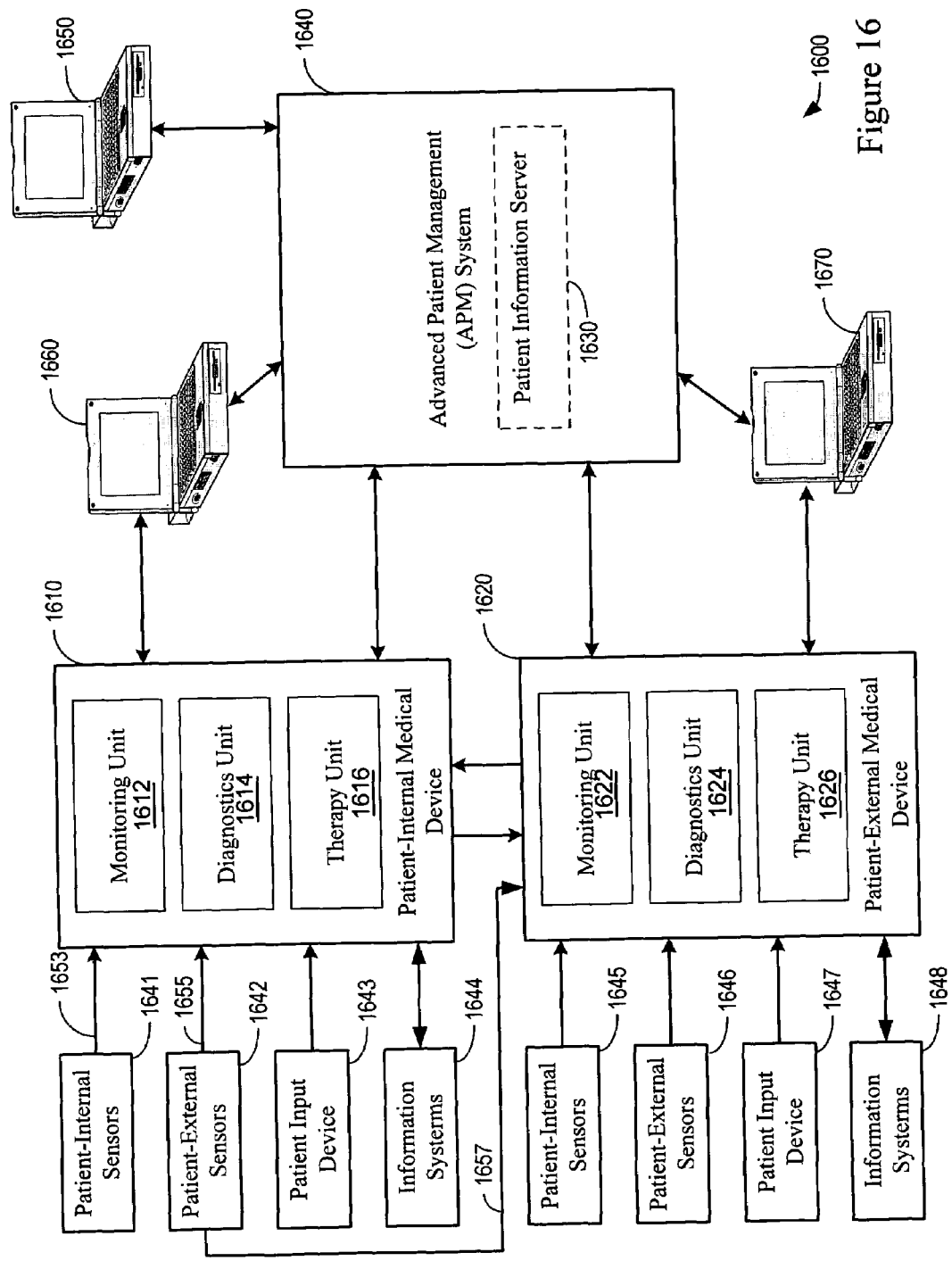
FIG. 16 is a block diagram of a medical system that may be used to implement coordinated patient monitoring, diagnosis, and/or therapy in accordance with embodiments of the present invention.

FIG. 16 is a block diagram of a medical system 1600 that may be used to implement coordinated patient measuring and/or monitoring, diagnosis, and/or therapy, including detecting snoring and determining the presence of sleep disordered breathing in accordance with embodiments of the invention. The medical system 1600 may include, for example, one or more patient-internal medical devices 1610 and one or more patient-external medical devices 1620. Each of the patient-internal 1610 and patient-external 1620 medical devices may include one or more of a patient monitoring unit 1612, 1622, a diagnostics unit 1614, 1624, and/or a therapy unit 1616, 1626.

The patient-internal medical device 1610 is typically a fully or partially implantable device that performs measuring, monitoring, diagnosis, and/or therapy functions. The patient-external medical device 1620 performs monitoring, diagnosis and/or therapy functions external to the patient (i.e., not invasively implanted within the patient's body). The patient-external medical device 1620 may be positioned on the patient, near the patient, or in any location external to the patient. It is understood that a portion of a patient-external medical device 1620 may be positioned within an orifice of the body, such as the nasal cavity or mouth, yet may be considered external to the patient (e.g., mouth pieces/appliances, tubes/appliances for nostrils, or temperature sensors positioned in the ear canal).

The patient-internal and patient-external medical devices 1610, 1620 may be coupled to one or more sensors 1641, 1642, 1645, 1646, patient input devices 1643, 1647 and/or other information acquisition devices 1644, 1648. The sensors 1641, 1642, 1645, 1646, patient input devices 1643, 1647, and/or other information acquisition devices 1644, 1648 may be employed to detect conditions relevant to the monitoring, diagnostic, and/or therapeutic functions of the patient-internal and patient-external medical devices 1610, 1620.

The medical devices 1610, 1620 may each be coupled to one or more patient-internal sensors 1641, 1645 that are fully or partially implantable within the patient. The medical devices 1610, 1620 may also be coupled to patient-external sensors positioned on, near, or in a remote location with respect to the patient. The patient-internal and patient-external sensors are used to sense conditions, such as physiological or environmental conditions, that affect the patient.

The patient-internal sensors 1641 may be coupled to the patient-internal medical device 1610 through one or more internal leads 1653. In one example, as was described above with reference to FIG. 13, an internal endocardial lead system is used to couple cardiac electrodes to an implantable pacemaker or other cardiac rhythm management device. Still referring to FIG. 16, one or more patient-internal sensors 1641 may be equipped with transceiver circuitry to support wireless communications between the one or more patient-internal sensors 1641 and the patient-internal medical device 1610 and/or the patient-external medical device 1620.

The patient-external sensors 1642 may be coupled to the patient-internal medical device 1610 and/or the patient-external medical device 1620 through one or more internal leads 1655 or through wireless connections. An example of patient-external sensors 1642 useful for snoring detection includes, but is not limited to, vibration sensors, microphones, airflow sensors or other transducers that may be coupled to a facial mask of a CPAP device or otherwise be incorporated as part of the CPAP device. Patient-external sensors 1642 preferably communicate with the patient-internal medical device 1610 wirelessly. Patient-external sensors 1646 may be coupled to the patient-external medical device 1620 through one or more internal leads 1657 or through a wireless link.

The medical devices 1610, 1620 may be coupled to one or more patient input devices 1643, 1647. The patient input devices are used to allow the patient to manually transfer information to the medical devices 1610, 1620. The patient input devices 1643, 1647 may be particularly useful for inputting information concerning patient perceptions, such as how well the patient feels, and information such as patient smoking, drug use, or other activities that are not automatically sensed or detected by the medical devices 1610, 1620.

The medical devices 1610, 1620 may be connected to one or more information acquisition devices 1644, 1648, for example, a database that stores information useful in connection with the monitoring, diagnostic, or therapy functions of the medical devices 1610, 1620. For example, one or more of the medical devices 1610, 1620 may be coupled through a network to a patient information server 1630 that provides information about environmental conditions affecting the patient, e.g., the pollution index for the patient's location.

In one embodiment, the patient-internal medical device 1610 and the patient-external medical device 1620 may communicate through a wireless link between the medical devices 1610, 1620. For example, the patient-internal and patient-external devices 1610, 1620 may be coupled through a short-range radio link, such as Bluetooth, IEEE 802.11, and/or a proprietary wireless protocol. The communications link may facilitate unidirectional or bi-directional communication between the patient-internal 1610 and patient-external 1620 medical devices. Data and/or control signals may be transmitted between the patient-internal 1610 and patient-external 1620 medical devices to coordinate the functions of the medical devices 1610, 1620.

In another embodiment, the patient-internal and patient-external medical devices 1610, 1620 may be used within the structure of an advanced patient management system 1640. Advanced patient management systems 1640 involve a system of medical devices that are accessible through various communications technologies. For example, patient data may be downloaded from one or more of the medical devices periodically or on command, and stored at the patient information server 1630. The physician and/or the patient may communicate with the medical devices and the patient information server 1630, for example, to acquire patient data or to initiate, terminate or modify therapy.

The data stored on the patient information server 1630 may be accessible by the patient and the patient's physician through one or more terminals 1650, e.g., remote computers located in the patient's home or the physician's office. The patient information server 1630 may be used to communicate to one or more of the patient-internal and patient-external medical devices 1610, 1620 to provide remote control of the monitoring, diagnosis, and/or therapy functions of the medical devices 1610, 1620.

In one embodiment, the patient's physician may access patient data transmitted from the medical devices 1610, 1620 to the patient information server 1630. After evaluation of the patient data, the patient's physician may communicate with one or more of the patient-internal or patient-external devices 1610, 1620 through the APM system 1640 to initiate, terminate, or modify the monitoring, diagnostic, and/or therapy functions of the patient-internal and/or patient-external medical systems 1610, 1620. Systems and methods involving advanced patient management techniques are further described in U.S. Pat. Nos. 6,336,903, 6,312,378, 6,270,457, and 6,398,728, hereby incorporated herein by reference.

In another embodiment, the patient-internal and patient-external medical devices 1610, 1620 may not communicate directly, but may communicate indirectly through the APM system 1640. In this embodiment, the APM system 1640 may operate as an intermediary between two or more of the medical devices 1610, 1620. For example, data and/or control information may be transferred from one of the medical devices 1610, 1620 to the APM system 1640. The APM system 1640 may transfer the data and/or control information to another of the medical devices 1610, 1620.

In one embodiment, the APM system 1640 may communicate directly with the patient-internal and/or patient-external medical devices 1610, 1620. In another embodiment, the APM system 1640 may communicate with the patient-internal and/or patient-external medical devices 1610, 1620 through medical device programmers 1660, 1670 respectively associated with each medical device 1610, 1620.

Various embodiments described herein may be used in connection with advanced patient management. Methods, structures, and/or techniques described herein relating to advanced patient management, such as those involving remote patient/device monitoring, diagnosis, therapy, or other advanced patient management related methodologies, may incorporate features of one or more of the following references: U.S. Pat. Nos. 6,221,011; 6,277,072; 6,280,380; 6,358,203; 6,368,284; and 6,440,066 each hereby incorporated herein by reference.

A number of the examples presented herein involve block diagrams illustrating functional blocks used for coordinated monitoring, diagnosis and/or therapy functions in accordance with embodiments of the present invention. It will be understood by those skilled in the art that there exist many possible configurations in which these functional blocks can be arranged and implemented. The examples depicted herein provide examples of possible functional arrangements used to implement the approaches of the invention.

Each feature disclosed in this specification (including any accompanying claims, abstract, and drawings), may be replaced by alternative features having the same, equivalent or similar purpose, unless expressly stated otherwise. Thus, unless expressly stated otherwise, each feature disclosed is one example only of a generic series of equivalent or similar features.

Various modifications and additions can be made to the preferred embodiments discussed hereinabove without departing from the scope of the present invention. Accordingly, the scope of the present invention should not be limited by the particular embodiments described above, but should be defined only by the claims set forth below and equivalents thereof.

What is claimed is:

1. A method of detecting snoring in a patient, comprising:
    generating a signal modulated by snoring using a sensor mechanically coupled to an external respiration therapy device; and
    detecting snoring based on the generated signal, wherein at least one of generating the signal and detecting snoring is performed using a component disposed in or on a cardiac rhythm management device.

2. The method of claim 1, wherein detecting snoring is performed implantably.

3. The method of claim 1, further comprising computing a snoring index developed from the detected snoring.

4. The method of claim 1, wherein detecting snoring comprises detecting snoring using circuitry disposed in or on the cardiac rhythm management device.

5. The method of claim 1, further comprising delivering a therapy to mitigate the detected snoring.

6. The method of claim 1, further comprising detecting sleep disordered breathing based on the detected snoring.

7. The method of claim 6, further comprising delivering a therapy to treat the detected disordered breathing.

8. The method of claim 1, further comprising predicting sleep disordered breathing based on the detected snoring.

9. The method of claim 8, further comprising delivering a therapy to treat the predicted disordered breathing.

10. The method of claim 1, further comprising evaluating one or both of sleepiness or hypertension based on the detected snoring.

11. The method of claim 1, further comprising transmitting information related to the detected snoring to a patient-external device.

12. The method of claim 1, further comprising displaying information related to the detected snoring.

13. A system for detecting snoring in a patient, comprising:
- a sensor configured to generate a signal modulated by snoring, the sensor disposed within or on an external respiration therapy device; and
- a processor configured to detect snoring using the snoring signal, wherein at least one of the sensor and the processor comprises a component disposed in or on a cardiac rhythm management device.

14. The system of claim 13, wherein the sensor comprises one or more of an accelerometer, a subsonic sensor, or a vibration sensor.

15. The system of claim 13, wherein the sensor comprises one or both of a microphone or a pressure transducer.

16. The system of claim 13, wherein the sensor comprises a respiration sensor.

17. The system of claim 13, further comprising a display device configured to display information related to the detected snoring.

18. The system of claim 13, further comprising a diagnostics unit configured to characterize one or more disorders based on the detected snoring.

19. The system of claim 13, wherein the processor is further configured to compute a snoring index based on the detected snoring.

20. The system of claim 13, wherein the sensor is mechanically coupled to a respiratory mask.

21. The system of claim 13, wherein the processor is disposed within or on an external respiratory therapy device.

22. The system of claim 13, further comprising a disordered breathing detector coupled to the processor and configured to predict or detect disordered breathing based on the detected snoring.

23. The system of claim 13, further comprising:
- a disordered breathing detector coupled to the processor and configured to predict or detect disordered breathing based on the detected snoring; and
- a therapy unit configured to deliver a therapy to treat the predicted or detected disordered breathing.

24. The system of claim 23, wherein the therapy unit comprises an external respiration therapy device.

25. The system of claim 23, wherein the therapy unit comprises a cardiac pulse generator.

* * * * *